(12) United States Patent
Lin et al.

(10) Patent No.: US 11,840,508 B2
(45) Date of Patent: Dec. 12, 2023

(54) CATALYST SYSTEM FOR OLEFIN POLYMERIZATION AND USE THEREOF

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Jie Lin, Beijing (CN); Xiaofan Zhang, Beijing (CN); Ting Huang, Beijing (CN); Junhui Zhang, Beijing (CN); Junling Zhou, Beijing (CN); Zhufang Sun, Beijing (CN); Xianzhi Xia, Beijing (CN); Hui Zhao, Beijing (CN); Zifang Guo, Beijing (CN); Jin Zhao, Beijing (CN); Haitao Liu, Beijing (CN); Meiyan Fu, Beijing (CN); Jigui Zhang, Beijing (CN); Lin Qi, Beijing (CN); Lian Yan, Beijing (CN); Wei Cen, Beijing (CN); Yu Wang, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 24 days.

(21) Appl. No.: 17/629,300

(22) PCT Filed: Jul. 24, 2020

(86) PCT No.: PCT/CN2020/104513
§ 371 (c)(1),
(2) Date: Jan. 21, 2022

(87) PCT Pub. No.: WO2021/018042
PCT Pub. Date: Feb. 4, 2021

(65) Prior Publication Data
US 2022/0251016 A1 Aug. 11, 2022

(30) Foreign Application Priority Data

Jul. 26, 2019 (CN) .......................... 201910684053.2
Jul. 26, 2019 (CN) .......................... 201910684095.6
Jul. 26, 2019 (CN) .......................... 201910684103.7
Jul. 26, 2019 (CN) .......................... 201910684239.8

(51) Int. Cl.
*C07C 43/21* (2006.01)
*C08F 10/06* (2006.01)
*C08F 10/00* (2006.01)
*C08F 110/02* (2006.01)
*C08F 210/06* (2006.01)
*C07C 47/575* (2006.01)
*C08F 110/06* (2006.01)

(52) U.S. Cl.
CPC ............ *C07C 47/575* (2013.01); *C07C 43/21* (2013.01); *C08F 110/06* (2013.01); *C07C 2603/92* (2017.05)

(58) Field of Classification Search
CPC ..... C07C 43/21; C07C 43/2603; C07C 43/92; C07C 2603/92; C08F 10/06; C08F 10/00; C08F 110/02; C08F 210/06
See application file for complete search history.

(56) References Cited

U.S. PATENT DOCUMENTS 4,540,679 A 9/1985 Arzoumanidis et al.
6,020,279 A 2/2000 Uwai et al.

FOREIGN PATENT DOCUMENTS

CN 85100997 A 1/1987
CN 1091748 A 9/1994
CN 1463990 A 12/2003

(Continued)

*Primary Examiner* — Catherine S Branch
(74) *Attorney, Agent, or Firm* — NKL Law; Allen Xue

(57) ABSTRACT

A catalyst system for olefin polymerization contains a main catalyst and a cocatalyst. The cocatalyst contains a twelve-membered ring compound represented by formula (M). The catalyst system is suitable for preparing polypropylene products having high stereoregularity and low ash, and can regulate the melt index of the products within a wide range by adjusting the amount of hydrogenation. It is also suitable for copolymerization systems to improve the copolymerization yield.

28 Claims, No Drawings

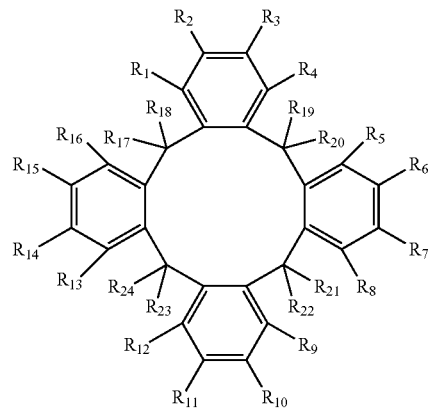

Formula (M)

(56) References Cited

FOREIGN PATENT DOCUMENTS

| | | |
|---|---|---|
| CN | 1506384 A | 6/2004 |
| CN | 1580136 A | 2/2005 |
| CN | 1330086 C | 8/2007 |
| CN | 101965369 A | 2/2011 |
| CN | 102399326 A | 4/2012 |
| CN | 110016093 A | 7/2019 |
| CN | 110016094 A | 7/2019 |
| JP | 2006206830 A | 8/2006 |
| WO | 03002617 A1 | 1/2003 |

CATALYST SYSTEM FOR OLEFIN POLYMERIZATION AND USE THEREOF

CROSS-REFERENCE TO RELATED APPLICATIONS

This application is a U.S. national entry of PCT International Application No. PCT/CN2020/104513, filed Jul. 24, 2020, which claims the priority of the following applications submitted on Jul. 26, 2019:
1. Chinese patent application CN201910684095.6, entitled "Twelve-membered ring compound and application thereof";
2. Chinese patent application CN 201910684053.2, entitled "Catalyst system for olefin polymerization and application thereof";
3. Chinese patent application CN 201910684239.8, entitled "Catalyst for olefin polymerization and olefin polymerization method"; and
4. Chinese patent application CN 201910684103.7, entitled "Catalyst system for olefin polymerization reaction and prepolymerization catalyst composition".

Contents of the above-listed applications are incorporated herein in their entireties by reference.

FIELD OF THE INVENTION

The present invention relates to the petrochemical field, and in particular, to a catalyst system for olefin polymerization and an olefin polymerization method.

BACKGROUND OF THE INVENTION

As is well-known, when a solid titanium catalyst component with magnesium, titanium, halogen and an electron donor compound as basic ingredients is used in an olefin polymerization reaction, due to the different characteristics of a different electron donor, some catalyst systems have relatively high catalytic activity; some catalyst systems have relatively good hydrogen modulation sensitivity; and some catalyst systems have relatively high stereospecificity. The industrial production of olefin polymer greatly requires a catalyst with excellent comprehensive properties, especially with high activity and high hydrogen modulation sensitivity simultaneously with high stereospecificity. The stereospecificity of the catalyst determines the isotactic index of a polymer, and the isotactic index is an important property index of the polymer. The higher the isotactic index of polypropylene is, the higher the degree of regularity and the crystallinity thereof are. Mechanical properties of the product such as hardness, stiffness, modulus, fracture, yield strength, etc. have all been increased, and melting point, thermal stability, aging resistance and radiation resistance have also been improved accordingly. Therefore, in order to improve the stereospecificity of the catalyst, researchers have been conducting a lot of research work. In some research, compounding two (or more than two) electron donors is used to make up for the shortcomings of a single electron donor, thereby improving the properties of the catalyst. However, the effect of the compounding is not a simple superposition of the properties of several electron donors. For example, WO03002617 discloses a catalyst component and a catalyst for olefin polymerization obtainable by using a monocarboxylic acid ester and a dicarboxylic acid ester in conjunction. This catalyst has good hydrogen modulation sensitivity, but its stereospecificity and polymerization activity are still not very high.

Therefore, it is still a problem to be solved urgently that a catalyst with excellent comprehensive properties is developed, that is, a catalyst with relatively high stereospecificity while maintaining high activity, so that the olefin polymer has a relatively high isotactic index and relatively low ash.

SUMMARY OF THE INVENTION

The inventors of the invention have found that by introducing a twelve-membered ring compound with a specific structure as a cocatalyst in the olefin polymerization process, and using it in conjunction with a Ziegler Natta-type main catalyst, the polymerization activity and stereospecificity of the catalyst can be significantly improved. Based on this finding, the invention is proposed.

In a first aspect, the invention provides a catalyst system for olefin polymerization, which includes a main catalyst and a cocatalyst, wherein the cocatalyst includes a twelve-membered ring compound represented by formula (M),

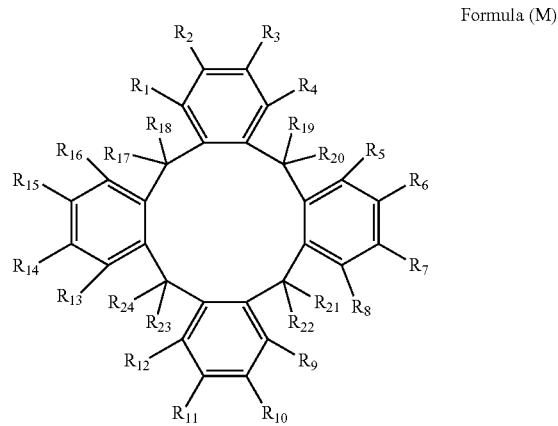

Formula (M)

wherein, in the formula (M), $R_1$-$R_{16}$ are the same or different, each independently selected from a group consisting of hydrogen, hydroxyl, halogen, cyano, nitro, amino, amine, aldehyde, carboxyl, ketone, alkoxy and hydrocarbyl, and when two adjacent groups on a benzene ring are each selected from a group consisting of alkoxy and hydrocarbyl, the two adjacent groups may optionally form a ring with each other, the ring selected from a group consisting of a saturated or unsaturated monocyclic ring, a saturated or unsaturated polycyclic ring and a combination thereof; $R_{17}$ to $R_{24}$ are the same or different, each independently selected from a group consisting of hydrogen and $C_1$-$C_{10}$ hydrocarbyl; and the amine, aldehyde, carboxyl, ketone, alkoxy and hydrocarbyl may be optionally substituted by one or more substituents.

In this application, "optional" or "optionally" indicates that the object described is or is not present.

According to an embodiment of the catalyst system of the invention, the main catalyst includes (i) a solid catalyst component containing magnesium, titanium, halogen and an internal electron donor compound, and (ii) an organic aluminum compound; and optionally (iii) an external electron donor compound. "Optionally (iii) an external electron donor compound" indicates that "(iii) an external electron donor compound" may or may not be present in the main catalyst.

According to some embodiments of the catalyst system of the invention, the main catalyst contains the external electron donor compound. According to some other embodiments of the catalyst system of the invention, the main catalyst does not contain the external electron donor compound.

According to an embodiment of the catalyst system of the invention, in the formula (M), $R_1$-$R_{16}$ are the same or different, each independently selected from a group consisting of hydrogen, hydroxyl, halogen, cyano, nitro, amino, mono-$C_1$-$C_{10}$ alkyl amine, bis-$C_1$-$C_{10}$ alkyl amine, $C_1$-$C_{10}$ aldehyde, $C_1$-$C_{10}$ carboxyl, $R_aC(O)$—, $R_aO$—, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl, and when two adjacent groups on a benzene ring are each selected from a group consisting of $R_aC(O)$—, $R_aO$—, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl, the two adjacent groups may optionally form a ring with each other, the ring selected from a group consisting of a saturated or unsaturated monocyclic ring, a saturated or unsaturated polycyclic ring and a combination thereof.

According to an embodiment of the catalyst system of the invention, in the formula (M), $R_a$ is selected from a group consisting of $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl.

According to an embodiment of the catalyst system of the invention, in the formula (M), $R_{17}$ to $R_{24}$ are the same or different, and are each independently selected from a group consisting of hydrogen, $C_1$-$C_{10}$ alkyl, $C_2$-$C_{10}$ alkenyl, $C_2$-$C_{10}$ alkynyl, $C_3$-$C_8$ cycloalkyl, $C_6$-$C_{10}$ aryl, $C_7$-$C_{20}$ aralkyl, 4-12-membered heterocycloalkyl and $C_5$-$C_{20}$ heteroaryl.

According to an embodiment of the catalyst system of the invention, in the formula (M), any one of the alkyl, alkenyl, alkynyl, cycloalkyl, aryl, aralkyl, heterocycloalkyl and heteroaryl may be optionally substituted by one or more substituents.

According to an embodiment of the catalyst system of the invention, in the formula (M), the substituents are selected from a group consisting of alkyl, alkoxyl, hydroxyl, halogen, cyano, nitro, amino, alkyl substituted amino, aldehyde, carboxyl and a heteroatom-containing group. Preferably, the substituents are selected from a group consisting of $C_1$-$C_{10}$ alkyl, $C_1$-$C_{10}$ alkoxyl, hydroxyl, halogen, cyano, nitro, amino, mono-$C_1$-$C_{10}$ alkyl amine, bis-$C_1$-$C_{10}$ alkyl amine, $C_1$-$C_{10}$ aldehyde, $C_1$-$C_{10}$ carboxyl and a heteroatom-containing group. More preferably, the substituents are selected from a group consisting of $C_1$-$C_6$ alkyl, $C_1$-$C_6$ alkoxyl, hydroxyl, fluorine, chlorine, bromine, iodine, cyano, nitro, amino, mono-$C_1$-$C_6$ alkyl amine, bis-$C_1$-$C_6$ alkyl amine, $C_1$-$C_6$ aldehyde and $C_1$-$C_6$ carboxyl.

According to an embodiment of the catalyst system of the invention, in the formula (M), $R_1$ to $R_{16}$ are the same or different, and are each independently selected from a group consisting of hydrogen, hydroxyl, halogen, cyano, nitro, amino, mono-$C_1$-$C_6$ alkyl amine, bis-$C_1$-$C_6$ alkyl amine, $C_1$-$C_6$ aldehyde, $C_1$-$C_6$ carboxyl, $R_aC(O)$—, $RaO$—, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $C_7$-$C_{10}$ aralkyl, 4-6-membered heterocycloalkyl and $C_5$-$C_{10}$ heteroaryl, wherein $R_a$ is selected from a group consisting of $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $C_7$-$C_{10}$ aralkyl, 4-6-membered heterocycloalkyl and $C_5$-$C_{10}$ heteroaryl.

According to an embodiment of the catalyst system of the invention, in the formula (M), $R_1$ to $R_{16}$ are the same or different, and are each independently selected from a group consisting of hydrogen, hydroxyl, amino, halogen, $C_1$-$C_6$ aldehyde, $C_1$-$C_6$ alkoxyl and halogen substituted $C_1$-$C_6$ alkoxyl.

According to an embodiment of the catalyst system of the invention, in the formula (M), $R_1$ to $R_{16}$ are not hydrogen at the same time.

According to an embodiment of the catalyst system of the invention, in the formula (M), $R_1$, $R_4$, $R_5$, $R_8$, $R_9$, $R_{12}$, $R_{13}$ and $R_{16}$ are each independently selected from a group consisting of hydrogen and $C_1$-$C_6$ alkyl. $R_2$, $R_3$, $R_6$, $R_7$, $R_{10}$, $R_{11}$, $R_{14}$ and $R_{15}$ are each independently selected from a group consisting of hydroxyl, amino, halogen, $C_1$-$C_6$ aldehyde, $C_1$-$C_6$ alkoxyl, and halogen substituted $C_1$-$C_6$ alkoxyl.

According to an embodiment of the catalyst system of the invention, in the formula (M), $R_{17}$ to $R_{24}$ are each independently selected from a group consisting of hydrogen and $C_1$-$C_{10}$ alkyl, preferably selected from a group consisting of hydrogen and $C_1$-$C_6$ alkyl, and more preferably selected from a group consisting of hydrogen and $C_1$-$C_4$ alkyl.

According to some examples, in the formula (M), $R_{17}$ to $R_{24}$ are all hydrogen, and the general formula is as follows,

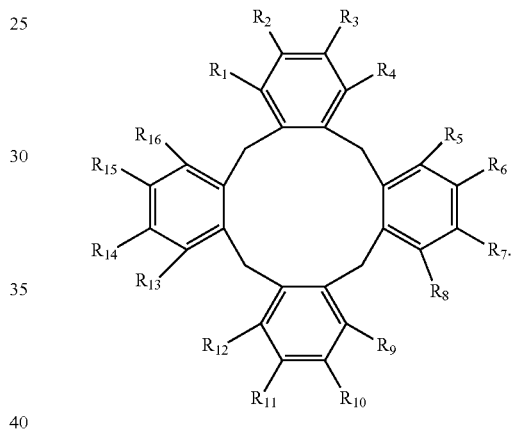

According to an embodiment of the catalyst system of the invention, the twelve-membered ring compound represented by the formula (M) is represented by formula (N), Formula (N)

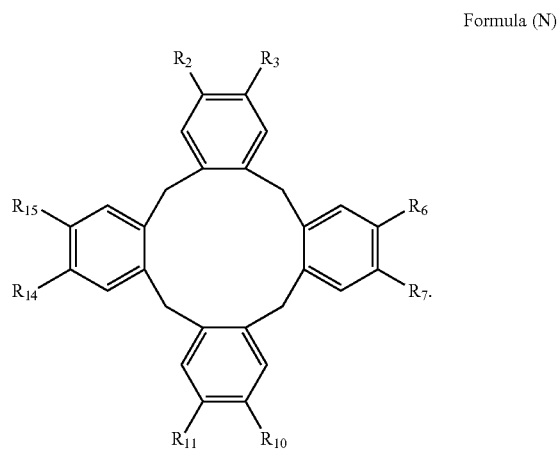

Specifically, the twelve-membered ring compound represented by the formula (M) may be selected from one or more of the following compounds:

Compound A: in the formula (N), $R_2=R_3=R_6=R_7=R_{10}=R_{11}=R_{14}=R_{15}=OCH_3$;

Compound B: in the formula (N), $R_2=R_3=R_6=R_7=R_{10}=R_{11}=R_{14}=R_{15}=OCH_2CH_3$;

Compound C: in the formula (N), $R_2=R_3=R_6=R_7=R_{10}=R_{11}=R_{14}=R_{15}=OCH_2CH_2CH_3$;

Compound D: in the formula (N), $R_2=R_3=R_6R_7=R_{10}=R_{11}=R_{14}=R_{15}=OCH(CH_3)_2$;

Compound E: in the formula (N), $R_2=R_3=R_6=R_7=R_{10}=R_{11}=R_{14}=R_{15}=OCH_2CH_2CH_2CH_3$;

Compound F: in the formula (N), $R_2=R_6=R_{10}=R_{14}=OCH_3$ and $R_3=R_7=R_{11}=R_{15}=OCH_2CH_3$;

Compound G: in the formula (N), $R_2=R_6=R_{10}=R_{14}=OCH_3$ and $R_3=R_7=R_{11}=R_{15}=OCH_2CH_2CH_3$;

Compound H: in the formula (N), $R_2=R_6=R_{10}=R_{14}=OCH_3$ and $R_3=R_7=R_{11}=R_{15}=OCH_2CH_2CH_2CH_3$;

Compound I: in the formula (N), $R_2=R_3=R_6=R_7=R_{10}=R_{11}=R_{14}=R_{15}=OH$;

Compound J: in the formula (N), $R_2=R_6=R_{10}=R_{14}=OCH_3$ and $R_3=R_7=R_{11}=R_{15}=OH$;

Compound K: in the formula (N), $R_2=R_6=R_{10}=R_{14}=OCH_3$ and $R_3=R_7=R_{11}=R_{15}=NH_2$;

Compound L: in the formula (N), $R_2=R_6=R_{10}=R_{14}=OCH_3$ and $R_3=R_7=R_{11}=R_{15}=Cl$;

Compound M: in the formula (N), $R_2=R_6=R_{10}=R_{14}=OCH_3$ and $R_3=R_7=R_{11}=R_{15}=Br$;

Compound N: in the formula (N), $R_2=R_6=R_{10}=R_{14}=OCH_3$ and $R_3=R_7=R_{11}=R_{15}=I$;

Compound O: in the formula (N), $R_2=R_6=R_{10}=R_{14}=OCH_3$ and $R_3=R_7=R_{11}=R_{15}=CHO$;

Compound P: in the formula (N), $R_2=R_6=R_{10}=R_{14}=OCH_3$ and $R_3=R_7=R_{11}=R_{15}=OCH_2CH_2CH_2Br$;

Compound Q: in the formula (N), $R_2=R_3=R_6=R_7=R_{10}=R_{11}=R_{14}=R_{15}=OCH_2CH_2Cl$; and Compound R: in the formula (N), $R_2=R_6=R_{10}=R_{14}=OH$ and $R_3=R_7=R_{11}=R_{15}=OCH_2CH_3$.

According to an embodiment of the catalyst system of the invention, the internal electron donor compound is selected from one or more of an aromatic carboxylic acid ester compound, a diether compound, an alcohol ester compound, a succinate compound and a ketone compound.

According to an embodiment of the catalyst system of the invention, the internal electron donor compound includes an alcohol ester compound and one or more compounds selected from a group consisting of a diether compound, an aromatic carboxylic acid ester compound, a succinate compound and a ketone compound. According to an embodiment of the catalyst system of the invention, a molar ratio of the alcohol ester compound to the one or more compounds selected from a group consisting of a diether compound, an aromatic carboxylic acid ester compound, a succinate compound and a ketone compound is 1:(0.02-50).

According to an embodiment of the catalyst system of the invention, the internal electron donor compound includes a succinate compound and one or more compounds selected from a group consisting of a diether compound, an aromatic carboxylic acid ester compound, an alcohol ester compound and a ketone compound. According to some examples, a molar ratio of the succinate compound to the one or more compounds selected from a group consisting of a diether compound, an aromatic carboxylic acid ester compound, an alcohol ester compound and a ketone compound is 1:(0.02-50).

According to an embodiment of the catalyst system of the invention, the alcohol ester compound is a glycol ester compound represented by formula B,

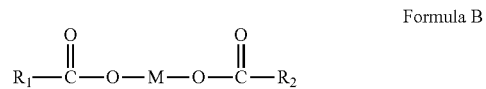

Formula B wherein, in the formula B, $R_1$ and $R_2$ are the same or different, each independently selected from a group consisting of $C_1$-$C_{20}$ alkyl, $C_2$-$C_{20}$ alkenyl, $C_3$-$C_{20}$ cycloalkyl, $C_6$-$C_{20}$ aryl, $C_7$-$C_{20}$ alkaryl, $C_7$-$C_{20}$ aralkyl and $C_{10}$-$C_{20}$ fused ring aryl, and preferably each independently selected from a group consisting of $C_1$-$C_{10}$ alkyl, $C_2$-$C_{10}$ alkenyl, $C_3$-$C_{10}$ cycloalkyl, $C_6$-$C_{10}$ aryl, $C_7$-$C_{10}$ alkaryl, $C_7$-$C_{10}$ aralkyl and Cm-Cis fused ring aryl, the alkyl, alkenyl, cycloalkyl, aryl, alkaryl, aralkyl and fused ring aryl optionally substituted by one or more substituents selected from a group consisting of $C_1$-$C_{10}$ alkyl, $C_1$-$C_{10}$ alkoxyl, hydroxyl, halogen, cyano, nitro, amino, mono-$C_1$-$C_6$ alkyl amine, bis-$C_1$-$C_6$ alkyl amine, aldehyde, carboxyl and a heteroatom; and M is a divalent linking group, preferably selected from a group consisting of $C_1$-$C_{20}$ alkylene, $C_3$-$C_{20}$ cycloalkylene and $C_6$-$C_{20}$ arylene, the alkylene, cycloalkylene and/or arylene substituted by a substituent selected from a group consisting of $C_1$-$C_{20}$ alkyl, $C_1$-$C_{20}$ alkoxyl and halogen, the substituent optionally bonded to form one or more rings, and the carbon atom or/and the hydrogen atom in M optionally substituted by a nitrogen, oxygen, sulfur, silicon, phosphorus or halogen atom.

According to some preferred embodiments of the invention, in the formula B, $R_1$ and $R_2$ are the same or different, and are each independently selected from a group consisting of $C_1$-$C_{10}$ alkyl, $C_2$-$C_{10}$ alkenyl, $C_2$-$C_{10}$ alkynyl, $C_3$-$C_{20}$ cycloalkyl, $C_6$-$C_{20}$ aryl, $C_7$-$C_{20}$ aralkyl and $C_7$-$C_{20}$ alkaryl, the alkyl, alkenyl, cycloalkyl, aryl, aralkyl or alkaryl optionally substituted by one or more substituents selected from a group consisting of halogen, $C_1$-$C_{10}$ alkyl and $C_1$-$C_{10}$ alkoxyl.

According to some preferred embodiments of the invention, in the formula B, M is selected from a group consisting of $C_1$-$C_{10}$ alkylene, $C_3$-$C_{10}$ cycloalkylene and $C_6$-$C_{10}$ arylene, the alkylene, cycloalkylene and/or the arylene optionally substituted by a substituent selected from a group consisting of $C_1$-$C_{10}$ alkyl, $C_1$-$C_{10}$ alkoxyl and halogen.

According to some examples, $R_1$ is phenyl or substituted phenyl, such as phenyl substituted by $C_1$-$C_6$ alkyl, $C_1$-$C_6$ alkoxyl, hydroxyl or halogen.

According to some examples, $R_2$ is phenyl or substituted phenyl, such as phenyl substituted by $C_1$-$C_6$ alkyl, $C_1$-$C_6$ alkoxyl, hydroxyl or halogen.

According to some examples, M is $C_1$-$C_{10}$ alkylene or substituted $C_1$-$C_{10}$ alkylene, such as alkylene substituted by $C_1$-$C_6$ alkyl, $C_1$-$C_6$ alkoxyl, hydroxyl or halogen.

According to some examples, M is benzylidene, substituted phenylene, naphthylene, or substituted naphthylene, such as phenylene or naphthylene substituted by $C_1$-$C_6$ alkyl, $C_1$-$C_6$ alkoxyl, hydroxyl or halogen.

According to some preferred embodiments of the invention, the alcohol ester compound is a glycol ester compound represented by formula C, Formula C

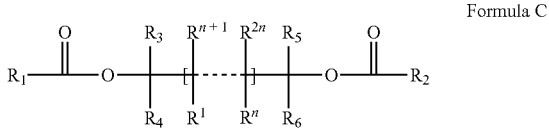

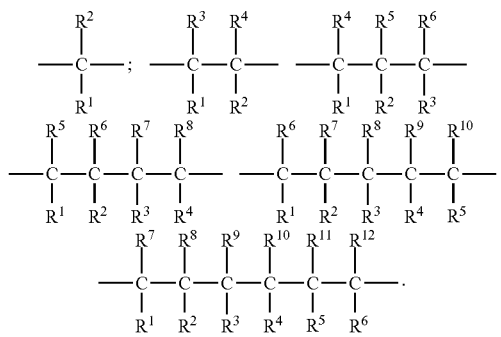

wherein, in the formula C, $R_1$ and $R_2$ are the same or different, and are each independently selected from a group consisting of $C_1$-$C_{10}$ alkyl, $C_2$-$C_{10}$ alkenyl, $C_2$-$C_{10}$ alkynyl, $C_3$-$C_{20}$ cycloalkyl, $C_6$-$C_{20}$ aryl, $C_7$-$C_{20}$ aralkyl and $C_7$-$C_{20}$ alkaryl, the alkyl, alkenyl, cycloalkyl, aryl, aralkyl or alkaryl optionally substituted by one or more substituents selected from a group consisting of halogen, $C_1$-$C_6$ alkyl and $C_1$-$C_6$ alkoxyl; $R_3$, $R_4$, $R_5$, $R_6$ and $R^1$-$R^{2n}$ are the same or different, and are each independently selected from a group consisting of hydrogen, halogen, $C_1$-$C_{20}$ alkyl, $C_2$-$C_{10}$ alkenyl, $C_2$-$C_{10}$ alkynyl, $C_3$-$C_{20}$ cycloalkyl, $C_6$-$C_{20}$ aryl, $C_7$-$C_{20}$ alkaryl, $C_7$-$C_{20}$ aralkyl and $C_{10}$-$C_{20}$ fused ring aryl, the alkyl, alkenyl, alkynyl, cycloalkyl, aryl, alkaryl, aralkyl and fused ring aryl optionally substituted by one or more substituents selected from a group consisting of halogen, $C_1$-$C_6$ alkyl and $C_1$-$C_6$ alkoxyl; $R_3$, $R_4$, $R_5$, $R_6$ and $R^1$-$R^{2n}$ optionally contain a heteroatom which is one or more of nitrogen, oxygen, sulfur, silicon, halogen and phosphorus; or, two or more of $R_3$, $R_4$, $R_5$, $R_6$ and $R^1$-$R^{2n}$ are bonded to each other to form a saturated or unsaturated monocyclic ring or a saturated or unsaturated polycyclic ring; wherein, n is an integer of 0-10, preferably an integer of 1-8, and more preferably an integer of 2-6, and when n is 0, the carbon atoms of the substituents $R_3$ and $R_4$ are bonded to the carbon atoms of the substituents $R_5$ and $R_6$. Those skilled in the art readily understand that the portion in the brackets,

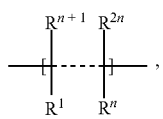

indicates that n carbon atoms are bonded, wherein each carbon atom is connected with two substituents, i.e., a portion composed of $R^1$, $R^2$, $R^3$ ... $R^{2n}$.

Those skilled in the art readily understand that when n is 0, the formula C is as follows:

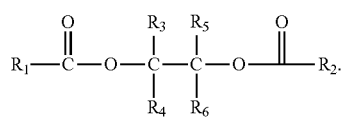

Those skilled in the art readily understand that n is 1, 2, 3, 4, 5 and 6,

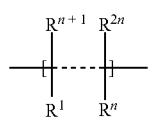

is respectively as follows:

According to some preferred embodiments of the invention, the alcohol ester compound is selected from a group consisting of 2,4-pentanediol dibenzoate, 3-methyl-2,4-pentanediol dibenzoate, 3,5-heptanediol dibenzoate, 4-ethyl-3,5-heptanediol dibenzoate, 3,5-heptanediol di-p-methyl benzoate, 3,5-heptanediol di-o-methyl benzoate, 3,5-heptanediol di-p-chlorobenzoate, 3,5-heptanediol di-o-chlorobenzoate, 3,5-heptanediol di-p-methoxy benzoate, 3,5-heptanediol di-o-methoxy benzoate, 3,5-heptanediol di-m-methoxy benzoate, 2-methyl-3,5-heptanediol dibenzoate, 4-methyl-3,5-heptanediol dibenzoate, 6-methyl-3,5-heptanediol dibenzoate, 4-ethyl-3,5-heptanediol dibenzoate, 5-ethyl-3,5-heptanediol dibenzoate, 4-propyl-3,5-heptanediol dibenzoate, 4-butyl-3,5-heptanediol dibenzoate, 2,4-dimethyl-3,5-heptanediol dibenzoate, 2,6-dimethyl-3,5-heptanediol dibenzoate, 4,4-dimethyl-3,5-heptanediol dibenzoate, 6,6-dimethyl-3,5-heptanediol dibenzoate, 4,6-dimethyl-3,5-heptanediol dibenzoate, 4,4-dimethyl-3,5-heptanediol dibenzoate, 6,6-dimethyl-3,5-heptanediol dibenzoate, 2-methyl-4-ethyl-3,5-heptanediol dibenzoate, 4-methyl-4-ethyl-3,5-heptanediol dibenzoate, 2-methyl-4-propyl-3,5-heptanediol dibenzoate, 4-methyl-4-propyl-3,5-heptanediol dibenzoate, 6-methyl-2,4-heptanediol bis(p-chlorobenzoic acid) ester, 6-methyl-2,4-heptanediol bis(p-toluic acid)ester, 6-methyl-2,4-heptanediol bis(m-toluic acid acid)ester, 2,2,6,6-tetramethyl-3,5-heptanediol dibenzoate, 4-methyl-3,5-octanediol dibenzoate, 4-ethyl-3,5-octanediol dibenzoate, 4-propyl-3,5-octanediol dibenzoate, 4-butyl-3,5-octanediol dibenzoate, 4,4-dimethyl-3,5-octanediol dibenzoate, 4-methyl-4-ethyl-3,5-octanediol dibenzoate, 2-methyl-4-ethyl-3,5-octanediol dibenzoate, 2-methyl-6-ethyl-3,5-octanediol dibenzoate, 5-methyl-4,6 nonanediol dibenzoate, 5-ethyl-4,6 nonanediol dibenzoate, 5-propyl-4,6 nonanediol dibenzoate, 5-butyl-4,6 nonanediol dibenzoate, 5,5-dimethyl-4,6 nonanediol dibenzoate, 5-methyl-4-ethyl-4,6 nonanediol dibenzoate, 5-phenyl-4,6-nonanediol dibenzoate, 4,6-nonanediol dibenzoate and 4-butyl-3,5-heptanediol dibenzoate, 1,2-phenylene dibenzoate, 3-methyl-5-tert-butyl-1,2-phenylene dibenzoate, 3,5-diisopropyl-1,2-phenylene dibenzoate, 3,6-dimethyl-1,2-phenylene dibenzoate, 4-tert-butyl-1,2-phenylene dibenzoate, 1,2-naphthalene dibenzoate, 2,3-naphthalene dibenzoate, dibenzoic acid-1,8-naphthyl ester, di-4-methylbenzoic acid-1,8-naphthyl ester, di-3-methylbenzoic acid-1,8-naphthyl ester, di-2-m ethylbenzoic acid-1,8-naphthyl ester, di-4-ethylbenzoic acid-1,8-naphthyl ester, di-4-n-propylbenzoic acid-1,8-naphthyl ester, di-4-isopropylbenzoic acid-1,8-naphthyl ester, di-4-n-butylbenzoic acid-1,8-naphthyl ester, di-4-isobutylbenzoic acid-1,8-naphthyl ester, di-4-tert-butylbenzoic acid-1,8-naphthyl ester, di-4-phenylbenzoic acid-1,8-naphthyl ester, di-4-fluorobenzoic acid-1,8-naphthyl ester, di-3-fluorobenzoic acid-1,8-naphthyl ester and di-2-fluorobenzoic acid-1,8-naphthyl ester.

According to an embodiment of the catalyst system of the invention, the structure of the aromatic carboxylic acid ester compound is as shown in formula F:

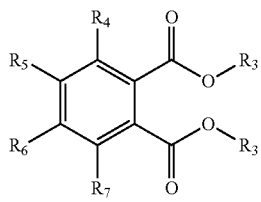

Formula F wherein, in the formula F, each $R_3$ is the same or different, which is independently $C_1$-$C_8$ alkyl, $C_5$-$C_{10}$ cycloalkyl, $C_6$-$C_{15}$ aryl, $C_7$-$C_{15}$ alkaryl or $C_7$-$C_{15}$ aralkyl, and hydrogen on the carbon of the $C_1$-$C_8$ alkyl, $C_3$-$C_{10}$ branched alkyl, $C_5$-$C_{10}$ cycloalkyl, $C_6$-$C_{15}$ aryl, $C_7$-$C_{15}$ alkaryl or $C_7$-$C_{15}$ aralkyl may be optionally substituted by a substituent selected from a group consisting of an alkane and a halogen atom, and preferably substituted by one or more substituents selected from a group consisting of $C_1$-$C_6$ alkyl, a fluorine atom, a chlorine atom, a bromine atom and an iodine atom; and $R_4$-$R_7$ may be the same or different, which are hydrogen, halogen, $C_1$-$C_6$ alkyl, $C_5$-$C_{10}$ cycloalkyl, $C_6$-$C_{20}$ aryl, $C_7$-$C_{20}$ alkaryl or $C_7$-$C_{20}$ aralkyl, and hydrogen on the carbon of the $C_1$-$C_8$ alkyl, $C_5$-$C_{10}$ cycloalkyl, $C_6$-$C_{15}$ aryl, $C_7$-$C_{15}$ alkaryl or $C_7$-$C_{15}$ aralkyl may be optionally substituted by a substituent selected from a group consisting of an alkane and a halogen atom, and preferably substituted by one or more substituents selected from a group consisting of $C_1$-$C_6$ alkyl, a fluorine atom, a chlorine atom, a bromine atom and an iodine atom.

According to a preferred embodiment of the invention, the aromatic carboxylic acid ester compound is a phthalic acid carboxylic acid ester.

According to a preferred embodiment of the invention, the aromatic carboxylic acid ester compound is selected from at least one of diethyl phthalate, dipropyl phthalate, diisobutyl phthalate, di-n-butyl phthalate, dipentyl phthalate, dihexyl phthalate, diheptyl phthalate and dioctyl phthalate.

According to an embodiment of the catalyst system of the invention, the structure of the succinate compound is as shown in formula G,

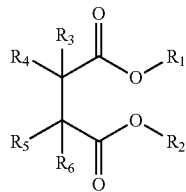

Formula G wherein, in the formula G, $R_1$ and $R_2$ are the same or different, each independently selected from a group consisting of a $C_1$-$C_{20}$ alkyl group, a $C_3$-$C_{20}$ cycloalkyl group, a $C_6$-$C_{20}$ aryl group, a $C_7$-$C_{20}$ arylalkyl group or a $C_7$-$C_{20}$ alkylaryl group, optionally containing a heteroatom; and $R_3$, $R_4$, $R_5$ and $R_6$ are the same or different, each independently selected from a group consisting of hydrogen, a $C_1$-$C_{20}$ alkyl group, a cycloalkyl group, an aryl group, an arylalkyl group or an alkylaryl group, optionally containing a heteroatom, and the groups may be connected to form a ring.

According to a preferred embodiment of the invention, in the formula G, $R_1$ and $R_2$ are the same or different, each independently selected from a group consisting of a $C_1$-$C_{10}$ alkyl group, a $C_3$-$C_{10}$ cycloalkyl group, a $C_6$-$C_{10}$ aryl group, a $C_7$-$C_{10}$ arylalkyl group or a $C_7$-$C_{10}$ alkylaryl group, optionally containing a heteroatom; and $R_3$, $R_4$, $R_5$ and $R_6$ are the same or different and are each independently selected from a group consisting of hydrogen, $C_1$-$C_{10}$ alkyl, $C_3$-$C_{10}$ cycloalkyl, $C_6$-$C_{10}$ aryl, $C_6$-$C_{10}$ arylalkyl or $C_6$-$C_{10}$ alkylaryl.

According to a preferred embodiment of the invention, the succinate compound is selected from a group consisting of 2,3-bis(2-ethylbutyl)diethyl succinate, 2,3-diethyl-2-isopropyl diethyl succinate, 2,3-diisopropyl diethyl succinate, 2,3-di-tert-butyl diethyl succinate, 2,3-diisobutyl diethyl succinate, 2,3-(bistrimethylsilyl) diethyl succinate, 2-(3,3,3-trifluoropropyl)-3-methyl diethyl succinate, 2,3-dineopentyl diethyl succinate, 2,3-diisopentyl diethyl succinate, 2,3-(1-trifluoromethyl-ethyl)diethyl succinate, 2-isopropyl-3-isobutyl diethyl succinate, 2-tert-butyl-3-isopropyl diethyl succinate, 2-isopropyl-3-cyclohexyl diethyl succinate, 2-isopentyl-3-cyclohexyl diethyl succinate, 2,2,3,3-tetramethyl diethyl succinate, 2,2,3,3-tetraethyl diethyl succinate, 2,2,3,3-tetrapropyl diethyl succinate, 2,3-diethyl-2,3-diisopropyl diethyl succinate, 2,3-diisobutyl bis(2-ethylbutyl) succinate, 2,3-diethyl-2-isopropyl diisobutyl succinate, 2,3-diisopropyl diisobutyl succinate, 2,3-di-tert-butyl diisobutyl succinate, 2,3-diisobutyl diisobutyl succinate, 2,3-(bistrimethylsilyl)diisobutyl succinate, 2-(3,3,3-trifluoropropyl)-3-diisobutyl methylsuccinate, 2,3-dineopentyl diisobutyl succinate, 2,3-diisopentyl diisobutyl succinate, 2,3-(1-trifluoromethyl-ethyl) diisobutyl succinate, 2-isopropyl-3-isobutyl diisobutyl succinate, 2-tert-butyl-3-isopropyl diisobutyl succinate, 2-isopropyl-3-cyclohexyl diisobutyl succinate, 2-isopentyl-3-cyclohexyl diisobutyl succinate, 2,2,3,3-tetramethyl diisobutyl succinate, 2,2,3,3-tetraethyl diisobutyl succinate, 2,2,3,3-tetrapropyl diisobutyl succinate and 2,3-diethyl-2,3-diisopropyl diisobutyl disuccinate; and preferably selected from a group consisting of 2,3-di isopropyl diethyl succinate, 2,3-di-tert-butyl diethyl succinate, 2,3-di isobutyl diethyl succinate and 2,3-diisopropyl diisobutyl succinate.

According to some embodiments, the external electron donor compound is selected from one or more of a silane compound, an ester compound, an ether compound, and a ketone compound, preferably, the compound is a diether compound.

According to an embodiment of the catalyst system of the invention, the structure of the silane compound is shown in formula D:

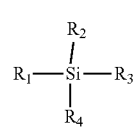

Formula D wherein in the formula D, $R_1$ to $R_4$ are the same or different, each independently selected from a group consisting of hydrogen, $C_1$-$C_{10}$ alkyl, $C_2$-$C_{10}$ alkenyl, alkoxyl, $C_2$-$C_{10}$ enyloxy, $C_2$-$C_{10}$ alkynyl, $C_2$-$C_{10}$ ynoxy, $C_3$-$C_{10}$ cycloalkyl, $C_6$-$C_{15}$ aryl, $C_3$-$C_{10}$ cycloalkoxyl, $C_6$-$C_{15}$ aryloxyl and amino, and the alkyl, alkenyl, alkynyl, alkoxyl, enyloxy, ynoxy, cycloalkyl, aryl, cycloalkoxyl, aryloxyl and amino may be optionally substituted by one or more substituents selected from a group consisting of halogen, $C_1$-$C_6$ alkyl, $C_3$-$C_6$ cycloalkyl, $C_6$-$C_{10}$ aryl and amino.

According to a preferred embodiment of the invention, in the formula D, $R_1$ to $R_4$ are the same or different, each independently selected from a group consisting of hydrogen, $C_1$-$C_6$ alkyl, $C_3$-$C_6$ cycloalkyl, $C_6$-$C_{10}$ aryl and amino, and the alkyl, cycloalkyl, aryl and amino may be optionally substituted by one or more substituents selected from a group consisting of halogen, $C_1$-$C_6$ alkyl, $C_3$-$C_6$ cycloalkyl, $C_6$-$C_{10}$ aryl and amino.

According to a preferred embodiment of the invention, the silane compound is selected from at least one of tetramethoxysilane, tetraethoxysilane, diisopropyldimethoxysilane, isopropyltrimethoxysilane, di-n-propyldimethoxysilane, n-propyltrimethoxysilane, di-n-butyldimethoxysilane, di-tert-butyl dim ethoxy silane, diisobutyldimethoxysilane, cyclopentyltrimethoxysilane, dicyclopentyldimethoxysilane, cyclohexylmethyldimethoxysilane, cyclohexyldimethoxysilane, cyclohexylethyldimethoxysilane, diphenyldimethoxysilane, diphenyldiethoxysilane, phenyltriethoxysilane, vinylmethoxysilane, vinylethoxysilane, vinylpropoxysilane, vinyldimethoxysilane, vinyldiethoxysilane, vinyldipropoxysilane, vinyltrimethoxysilane, vinyltriethoxysilane, vinyltripropoxysilane, allylmethoxysilane, allylethoxysilane, allylpropoxysilane, allyldimethoxysilane, allyldiethoxysilane, allyldipropoxysilane, allyltrimethoxysilane, allyltriethoxysilane, allyltripropoxysilane, aminotrimethylsilane, aminotriethylsilane, aminotripropylsilane, aminotri-n-butylsilane, aminotriisobutylsilane, methylaminotrimethylsilane, methylaminotriethylsilane, methylaminotripropylsilane, methylaminotri-n-butylsilane, methylaminotriisobutylsilane, ethylaminotrimethylsilane, ethylaminotriethylsilane, ethylaminotripropylsilane, ethylaminotri-n-butylsilane and ethylaminotriisobutylsilane.

According to an embodiment of the catalyst system of the invention, the diether compound that can be used as an internal electron donor compound and/or an external electron donor compound is a 1,3-diether compound represented by formula E,

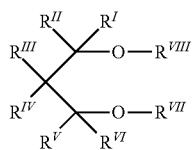

Formula E wherein, in the formula E, $R^I$, $R^{II}$, $R^{III}$, $R^{IV}$, $R^V$ and $R^{VI}$ are the same or different, and are each independently selected from a group consisting of hydrogen, halogen, $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl; $R^{VII}$ and $R^{VIII}$ are the same or different, and are each independently selected from a group consisting of $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, wherein any one of the alkyl, alkenyl, alkynyl, cycloalkyl, aryl, aralkyl and alkaryl may be optionally substituted by one or more substituents which are selected from a group consisting of hydroxyl, halogen, cyano, nitro, amino, mono-$C_1$-$C_{10}$ alkyl amine, bis-$C_1$-$C_{10}$ alkyl amine, aldehyde, carboxyl and a heteroatom; or, two or more of $R^I$, $R^{II}$, $R^{III}$, $R^{IV}$, $R^V$ and $R^{VI}$ are bonded to each other to form a saturated or unsaturated monocyclic or polycyclic ring, such as a fluorene ring.

According to a preferred embodiment of the invention, in the formula E, $R^I$, $R^{II}$, $R^{III}$, $R^{IV}$, $R^V$ and $R^{VI}$ are the same or different, and are each independently selected from a group consisting of hydrogen, halogen, $C_1$-$C_{18}$ alkyl, $C_3$-$C_{18}$ cycloalkyl, $C_6$-$C_{18}$ aryl, $C_7$-$C_{18}$ aralkyl and $C_7$-$C_{18}$ alkaryl.

According to a preferred embodiment of the invention, in the formula E $R^I$, $R^{II}$, $R^{III}$, $R^{IV}$, $R^V$ and $R^{VI}$ are the same or different, and are each independently selected from a group consisting of hydrogen, halogen, $C_1$-$C_{10}$ alkyl, $C_3$-$C_{10}$ cycloalkyl, $C_6$-$C_{10}$ aryl, $C_7$-$C_{10}$ aralkyl and $C_7$-$C_{10}$ alkaryl.

According to a preferred embodiment of the invention, in the formula E, $R^{VII}$ and $R^{VIII}$ are the same or different, and are each independently selected from a group consisting of hydrogen, halogen, $C_1$-$C_{10}$ alkyl, $C_3$-$C_{10}$ cycloalkyl, $C_6$-$C_{10}$ aryl, $C_7$-$C_{10}$ aralkyl and $C_7$-$C_{10}$ alkaryl.

According to a preferred embodiment of the invention, in the formula E, $R^{VII}$ and $R^{VIII}$ are each independently selected from a group consisting of hydrogen, halogen, $C_1$-$C_{10}$ alkyl, $C_3$-$C_{10}$ cycloalkyl, $C_6$-$C_{10}$ aryl, $C_7$-$C_{10}$ aralkyl and $C_7$-$C_{10}$ alkaryl.

According to a preferred embodiment of the invention, in the formula E, $R^{III}$ and $R^{IV}$ are bonded to each other to form a saturated or unsaturated monocyclic or polycyclic ring.

According to a preferred embodiment of the invention, in the formula E, $R^{VII}$ and $R^{VIII}$ are each independently $C_1$-$C_{10}$ alkyl.

According to a preferred embodiment of the invention, the diether compound is selected from at least one of 2-isopropyl-2-isopentyl-1,3-dimethoxypropane, 2-(2-ethylhexyl) 1,3-dimethoxypropane, 2-isopropyl-1,3-dimethoxypropane, 2-butyl-1,3-dimethoxypropane, 2-sec-butyl-1,3-dimethoxypropane, 2-cyclohexyl-1,3-dimethoxypropane, 2-phenyl-1,3-dimethoxypropane, 2-(2-phenylethyl)-1,3-dimethoxypropane, 2-(2-cyclohexylethyl)-1,3-dimethoxypropane, 2-(p-chlorophenyl)-1,3-dimethoxypropane, 2-(diphenylmethyl)-1,3-dimethoxypropane, 2-(1-naphthyl)-1,3-dimethoxypropane, 2-(2-fluorophenyl)-1,3-dimethoxypropane, 2,2-di cyclohexyl-1,3-dimethoxypropane, 2,2-dicyclopentyl-1,3-dimethoxypropane, 2,2-diethyl-1,3-dimethoxypropane, 2,2-dipropyl-1,3-dimethoxypropane, 2,2-diisopropyl-1,3-dimethoxypropane, 2,2-dibutyl-1,3-dimethoxypropane, 2-methyl-2-propyl-1,3-dimethoxypropane, 2-methyl-2-benzyl-1,3-dimethoxypropane, 2-methyl-2-ethyl-1,3-dimethoxypropane, 2-methyl-2-isopropyl-1,3-dimethoxypropane, 2-methyl-2-phenyl-1,3-dimethoxypropane, 2-methyl-2-cyclohexyl-1,3-dimethoxypropane, 2,2-bis(p-chlorophenyl)-1,3-dimethoxypropane, 2,2-bis(2-cyclohexylethyl)-1,3-dimethoxypropane, 2-methyl-2-isobutyl-1,3-dimethoxypropane, 2-methyl-2-(2-ethylhexyl)-1,3-dimethoxypropane, 2,2-diisobutyl-1,3-dimethoxypropane, 2,2-diphenyl-1,3-dimethoxypropane, 2,2-dibenzyl-1,3-dimethoxypropane, 2,2-bis(cyclohexylmethyl)-1,3-dimethoxypropane, 2-isobutyl-2-isopropyl-1,3-dimethoxypropane, 2-(1-methylbutyl)-2-isopropyl-1,3-dimethoxypropane, 2-(1-methylbutyl)-2-sec-butyl-1,3-dimethoxypropane, 2,2-di-sec-butyl-1,3-dimethoxypropane, 2,2-di-tert-butyl-1,3-dimethoxypropane, 2,2-dineopentyl-1,3-dimethoxypropane, 2-isopropyl-2-isopentyl-1,3-dimethoxypropane, 2-isopropyl-2-phenyl-1,3-dimethoxypropane, 2-phenyl-2-sec-butyl-1,3-dimethoxypropane, 2-isopropyl-2-benzyl-1,3-dimethoxypropane, 2-isopropyl-2-cyclopentyl-1,3-dimethoxypropane, 2-cyclopentyl-2-sec-butyl-1,3-dimethoxypropane, 2-cyclohexyl-2-isopropyl-1,3-dimethoxypropane, 2-sec-butyl-2-cyclohexyl-1,3- dimethoxypropane, 2-isopropyl-2-sec-butyl-1,3-dimethoxypropane, 2-cyclohexyl-2-cyclohexylmethyl-1,3-dimethoxypropane, 1,1-bis(methoxymethyl)-cyclopentadiene, 1,1-bis(methoxymethyl)-2,3,4,5,-tetramethylcyclopentadiene, 1,1-bis(methoxymethyl)-2,3,4,5,-tetramethylcyclopentadiene, 1,1-bis(methoxymethyl)-2,3,4,5,-tetraphenylcyclopentadiene, 1,1-bis(methoxymethyl)-2,3,4,5,-tetrafluorocyclopentadiene, 1,1-bis(methoxymethyl)-3,4-dicyclopentylcyclopentadiene, 1,1-bis(methoxymethyl)indene, 1,1-bis(methoxymethyl)-2,3-dimethoxyindene, 1,1-bis(methoxymethyl)-2,3,6,7-tetrafluoroindene, 1,1-bis(methoxymethyl)-4,5,6,7-tetrafluoroindene, 1,1-bis(methoxymethyl) 4,7-dimethylindene, 1,1-bis(methoxymethyl)-3,6-dimethylindene, 1,1-bis(methoxymethyl)-4-phenylindene, 1,1-bis(methoxymethyl)-4-phenyl-2-methylindene, 1,1-bis(methoxymethyl)-4-tetracyclohexylindene, 1,1-bis(methoxymethyl)-7-(3,3,3-trifluoropropyl)phenylindene, 1,1-bis(methoxymethyl)-7-cyclopentylindene, 1,1-bis(methoxymethyl)-7-isopropylindene, 1,1-bis(methoxymethyl)-7-cyclohexylindene, 1,1-bis(methoxymethyl)-7-tert-butylindene, 1,1-bis(methoxymethyl)-7-tert-butyl-2-methylindene, 1,1-bis(methoxymethyl)-7-phenylindene, 1,1-bis(methoxymethyl)-2-phenylindene, 9,9-bis(methoxymethyl)fluorene, 9,9-bis(methoxymethyl)-2,7-dicyclopentylfluorene, 9,9-bis(methoxymethyl)-1,8-dichlorofluorene, 9,9-bis(methoxymethyl)-1,8-difluorofluorene, 9,9-bis(methoxymethyl)-1,2,3,4-tetrahydrofluorene, 9,9-bis(methoxymethyl)-4-tert-butylfluorene, 1,1-bis-(methoxymethyl)-2,5-cyclohexadiene, 1,1-bis-(methoxymethyl)-benzonaphthalene, 7,7-bis-(methoxymethyl)-2,5-norbornadiene, 9,9-bis-(methoxymethyl)-1,4-methanedihydronaphthalene, 9,9-bis-(methoxymethyl)-1,4-methanedihydroanthracene, 4,4-bis-(methoxymethyl)-1-phenyl-1,4-dihydronaphthalene, 4,4-bis-(methoxymethyl)-1-phenyl-3,4-dihydronaphthalene, 5,5-bis-(methoxymethyl)-1,3,6-cycloheptatriene and 1-methoxymethyl-1-(1'-methoxyethyl)-2,3,4,5-tetramethyl-cyclopentadiene.

According to an embodiment of the catalyst system of the invention, a molar ratio of the twelve-membered ring compound represented by formula (M) to the external electron donor compound is 1:100-100:1, preferably 1:50-50:1, and more preferably 1:20-20:1.

According to an embodiment of the catalyst system of the invention, the organic aluminum compound is an alkyl aluminum compound. According to a preferred embodiment of the invention, the general formula of the alkyl aluminum compound is $AlR_3$, wherein each R is independently selected from a group consisting of hydrogen, halogen, $C_1$-$C_{20}$ alkyl, $C_1$-$C_{20}$ alkoxyl or halogenated $C_1$-$C_{20}$ alkyl, and at least one of three Rs is $C_1$-$C_{20}$ alkyl or halogenated $C_1$-$C_{20}$ alkyl. According to a preferred embodiment of the invention, the general formula of the alkyl aluminum compound is $AlR_3$, wherein each R is independently selected from a group consisting of hydrogen, halogen, $C_1$-$C_{10}$ alkyl, $C_1$-$C_{10}$ alkoxyl or halogenated $C_1$-$C_{10}$ alkyl, and at least one of three Rs is $C_1$-$C_{10}$ alkyl or halogenated $C_1$-$C_{10}$ alkyl. Specifically, the organic aluminum compound preferably includes one or more selected from a group consisting of trialkylaluminum, dialkylaluminum chloride, monoalkylaluminum dichloride, and alkylaluminoxane.

According to a preferred embodiment of the invention, the alkyl aluminum compound is one or more of triethyl aluminum, tri-n-propyl aluminum, tri-isopropyl aluminum, tri-n-butyl aluminum, tri-isobutyl aluminum, tri-n-hexyl aluminum, tri-n-octyl aluminum, triisobutyl aluminum, diethyl aluminum monohydrogen, diisobutyl aluminum monohydrogen, diethyl aluminum chloride, diisobutyl aluminum chloride, ethyl aluminum dichloride, $Al(n-C_6H_{13})_3$ and $Al(n-C_8H_{17})_3$.

According to an embodiment of the catalyst system of the invention, a molar ratio of the twelve-membered ring compound represented by formula (M) to the organic aluminum compound in terms of aluminum is 1:(0.1-500), and preferably 1:(1-200).

According to an embodiment of the catalyst system of the invention, a molar ratio of the solid catalyst component in terms of a titanium element to the organic aluminum compound in terms of aluminum is 1:(5-5000), and preferably 1:(20-2000).

According to some embodiments of the catalyst system of the invention, a molar ratio of the external electron donor compound to the titanium element in the solid catalyst component is (0-500): 1, preferably (0.01-200):1, and more preferably (0.1-100): 1.

According to an embodiment of the catalyst system of the invention, the weight ratio of the titanium element, the magnesium element, and the internal electron donor compound in the solid catalyst component is 1:(5-25):(2-15).

According to the invention, the solid catalyst component includes titanium, magnesium and an internal electron donor, and is a reaction product of a titanium compound, a magnesium compound and an internal electron donor.

In the invention, the method for preparing a solid catalyst component may be carried out according to a method conventionally used in the art. For example, reference may be made to the methods disclosed in CN1506384, CN1091748, CN85100997, CN102399326A, U.S. Pat. No. 4,540,679, etc., the disclosure of which is incorporated herein by reference.

In the invention, the method of preparing a solid catalyst component includes but is not limited to the following methods.

Method 1: An inert solvent is added to the magnesium compound followed by adding an organic epoxy compound and an organic phosphorus compound. After dissolving, a precipitation aid and a titanium compound are added to precipitate a solid. An internal electron donor is added to attach it to the solid, and then the treatment with titanium tetrahalide and an inert diluent is performed to obtain the solid catalyst component.

Method 2: In an inert solvent such as decane or toluene, etc., a solid magnesium compound is dissolved in an organic alcohol compound such as 2-ethylhexanol. After dissolving, a precipitation aid and a titanium compound are added to precipitate a solid. An internal electron donor is added to attach it to the solid, and then the treatment with the titanium compound and an inert diluent is performed to obtain the solid catalyst component.

Method 3: A magnesium halide alcoholate is dispersed into a titanium compound at a low temperature (for example, below −5° C.) followed by raising the temperature to a high temperature (for example, above 50° C.). An internal electron donor compound is added in the temperature raising process followed by filtration. The resulting precipitate is treated with a titanium compound and is washed to obtain the solid catalyst component.

Method 4: A magnesium alkoxide carrier and an inert diluent are formulated into a suspension, and then the suspension is reacted with a mixture formed by a titanium compound and an inert diluent followed by filtration. The resulting precipitate is contacted and reacted with the titanium compound and an internal electron donor compound. The precipitate is washed to obtain the solid catalyst component.

According to some embodiments of the invention, a titanium compound or a mixture of a titanium compound and an inert solvent (an inert solvent such as hexane, heptane, octane, decane, toluene, etc.) pre-cooled to −15° C. to −40° C. is mixed with a magnesium compound, and the temperature of the mixture is raised to 90-110° C. in stages and maintained for 0.1-2 hours. An internal electron donor is added in the temperature raising process. Then the solid-liquid separation is performed, and the resulting solid phase is treated with the titanium compound again for at least 2 times, washed with a solvent, and finally vacuum dried to obtain the solid catalyst component.

According to the invention, the magnesium compound may be various magnesium compounds conventionally used in the preparation of an olefin polymerization catalyst in the art. For example, the magnesium compound may be selected from at least one of magnesium dihalide, magnesium alkoxide, magnesium alkyl, a hydrate of magnesium dihalide, an alcoholate of magnesium dihalide, and a derivative in which one halogen atom in the magnesium dihalide molecule is substituted by alkoxy or halogenated alkoxy. According to a preferred embodiment of the invention, the magnesium compound is an alcoholate of magnesium dihalide.

According to a preferred embodiment of the invention, the alcoholate of magnesium dihalide has a spherical magnesium alcoholate represented by formula (I), $$MgX_2 \cdot m(R'OH) \cdot nE \cdot qH_2O \qquad \text{Formula (I)}$$

wherein, in the formula (I), X is chlorine or bromine; R' is $C_1$-$C_4$ alkyl (for example, methyl, ethyl, n-propyl, isopropyl, n-butyl, isobutyl and tert-butyl), and m is 0.5-4.0; E is an ether or ester electron donor compound, and n is 0-1.0, wherein the ether or ester may be an ether or ester known as an electron donor in the art, and may also be the internal electron donor and/or external electron donor used in the invention; and q is 0-0.8.

According to a preferred embodiment of the invention, in the formula (I), X is chlorine or bromine; R' is $C_1$-$C_4$ alkyl, and m is 1.5-3.5; and n and q are both zero.

According to a preferred embodiment of the invention, the magnesium compound is $MgCl_2 \cdot m(CH_3CH_2OH)$, and m is 1.5-3.5.

According to some embodiments of the invention, the preparation method of the alcoholate of magnesium dihalide may be performed according to a known method in the art. For example, reference may be made to the method disclosed in CN1330086A.

According to a preferred embodiment of the invention, the preparation method of the alcoholate of magnesium dihalide includes: (1) mixing anhydrous magnesium dihalide with an alcohol compound (R'OH), and performing the reaction at 90-140° C. to obtain an alcoholate of magnesium halide; (2) shearing the alcoholate of magnesium halide in a dispersion medium, and performing cooling in an inert medium after the shearing to obtain the spherical alcoholate of magnesium halide. The mixing ratio of the anhydrous magnesium dihalide and the alcohol compound may be determined according to the actually required ratio of the alcohol compound loaded on the anhydrous magnesium dihalide. The dispersion medium may be a hydrocarbon inert solvent, such as kerosene, white oil, silicone oil, paraffin oil, petroleum jelly and the like. The inert medium may be selected from a group consisting of pentane, hexane, heptane, petroleum ether, raffinate and the like. The shearing refers to the shearing of the alcoholate of magnesium halide by external shearing force, e.g., a high-speed stirring method (such as CN1330086), a spraying method (such as U.S. Pat. No. 6,020,279) and a supergravity rotating bed (such as CN1580136A) and an emulsifying pelletizer method (CN1463990A), etc.

According to a preferred embodiment of the invention, in order to further improve the purity of the magnesium compound, the resulting spherical alcoholate of magnesium halide is further subjected to washing and drying steps.

The magnesium alkoxide according to the invention is obtained by reacting metallic magnesium, ethanol, isooctyl alcohol (2-ethylhexanol) and a mixed halogenating agent under an inert atmosphere. The mixed halogenating agent is a combination of halogen and a halogen compound. The non-limiting selection of the halogen and the halogen compound includes iodine, bromine, chlorine, magnesium chloride, magnesium bromide, magnesium iodide, potassium chloride, potassium bromide, potassium iodide, calcium chloride, calcium bromide, calcium iodide, mercury chloride, mercury bromide, mercury iodide, ethoxymagnesium iodide, methoxymagnesium iodide, isopropylmagnesium iodide, hydrogen chloride, chloroacetyl chloride and so on.

According to the invention, the titanium compound may be various titanium compounds conventionally used in the preparation of an olefin polymerization catalyst in the art. According to a preferred embodiment of the invention, the titanium compound has a structure represented by formula (II), $$Ti(OR'')_{4-k}X_k \qquad \text{Formula (II)}$$

wherein, in the formula (II), R'' is $C_1$-$C_{20}$ alkyl, and X is F, Cl or Br; and k is an integer of 0-4.

According to a preferred embodiment of the invention, in the formula (II), R'' is $C_1$-$C_{10}$ alkyl.

According to a preferred embodiment of the invention, in the formula (II), R'' is $C_1$-$C_5$ alkyl.

According to a preferred embodiment of the invention, for example, in the formula (II), R'' is methyl, ethyl, n-propyl, isopropyl, n-butyl, isobutyl, tert-butyl, n-pentyl, isopentyl and neopentyl.

According to a preferred embodiment of the invention, in the formula (II), X is Cl.

According to a preferred embodiment of the invention, the titanium compound is selected from at least one of titanium tetrachloride, titanium tetrabromide, titanium tetraiodide, titanium tetrabutoxide, titanium tetraethoxide, titanium monochlorotributoxide, titanium chlorodibutoxide, titanium trichlorobutoxide, titanium monochlorotriethoxide, titanium dichlorodiethoxide, titanium trichloromonoethoxide and titanium trichloride.

According to a preferred embodiment of the invention, the titanium compound is titanium tetrachloride.

In a second aspect, the invention also provides a prepolymerized catalyst composition for olefin polymerization, which comprises the catalyst system described in the first aspect and a prepolymer obtained by olefin prepolymerization.

According to some embodiments of the invention, a prepolymerization multiple of the prepolymer is 0.1-1000 g olefin polymer/g solid catalyst component.

According to some preferred embodiments of the invention, a prepolymerization multiple of the prepolymer is 0.2-500 g olefin polymer/g solid catalyst component.

According to some preferred embodiments of the invention, a prepolymerization multiple of the prepolymer is 0.5-20 g olefin polymer/g solid catalyst component.

According to some embodiments of the invention, the temperature of the pre-polymerization is −20-80° C., and the polymerization pressure is preferably 0-5 MPa.

According to some preferred embodiments of the invention, the temperature of the prepolymerization is 0-50° C.

According to some embodiments of the invention, the prepolymerization is performed in a liquid or gas phase.

In a third aspect, the invention also provides a method for olefin polymerization, comprising: polymerizing an olefin in the presence of the catalyst system according to the first aspect and/or the prepolymerized catalyst composition according to the second aspect.

According to an embodiment of the method for olefin polymerization according to the invention, the general formula of the olefin is $CH_2=CHR$, wherein R is hydrogen or $C_1$-$C_8$ alkyl, and preferably hydrogen or $C_1$-$C_6$ alkyl. Preferably, the olefin is selected from one or more of ethylene, propylene, 1-butene, 4-methyl-1-pentene and 1-hexene. According to some examples, the olefin is ethylene, propylene, or a mixture of ethylene and propylene.

According to the invention, the catalyst system of the invention may be directly added to the reactor for use in the polymerization process, or the catalyst system and the prepolymerized catalyst composition obtained by olefin pre-polymerization are added to the reactor for the polymerization reaction.

According to the invention, the olefin polymerization reaction may be carried out according to a known polymerization method, may be carried out in a liquid phase or gas phase, may also be carried out under the operation of a combination of liquid phase and gas phase polymerization stages, and may also be carried out using conventional techniques such as a slurry method, a gas phase fluidized bed, etc.

According to some preferred embodiments of the invention, conditions of the polymerization include a temperature of 0-150° C., time of 0.2-5 hours, and a pressure of 0.01-10 MPa.

According to some preferred embodiments of the invention, conditions of the polymerization include a temperature of 50-90° C., time of 0.3-2 hours, and a pressure of 0.02-5 MPa.

According to the invention, the polymerization may be carried out in the presence of a solvent. In terms of the titanium element in the solid catalyst component, the concentration of the catalyst system in the solvent may be $0.1 \times 10^{-5}$–$5 \times 10^{-5}$ mol/L.

According to some preferred embodiments of the invention, in terms of the titanium element in the solid catalyst component, the concentration of the catalyst system in the solvent may be $0.2 \times 10^{-5}$–$2 \times 10^{-5}$ mol/L.

In the invention, hydrocarbyl may be selected from a group consisting of alkyl, cycloalkyl, alkenyl, alkynyl, aryl, aralkyl and alkaryl.

In the invention, alkyl refers to straight-chain alkyl or branched-chain alkyl, non-limiting examples of which include methyl, ethyl, n-propyl, isopropyl, n-butyl, sec-butyl, isobutyl, tert-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl and n-eicosyl.

In the invention, examples of alkenyl may include but are not limited to, vinyl, propenyl, butenyl, pentenyl and octenyl.

In the invention, examples of alkynyl may include but are not limited to, ethynyl and propargyl.

In the invention, examples of cycloalkyl may include but are not limited to, cyclopropyl, cyclobutyl, cyclopentyl, cyclohexyl, 4-methylcyclohexyl, 4-ethylcyclohexyl, 4-n-propylcyclohexyl, 4-n-butylcyclohexyl, cycloundecyl and cyclododecyl.

In the invention, examples of halogen include but are not limited to, fluorine, chlorine, bromine and iodine.

In the invention, examples of aryl may include but are not limited to, phenyl, methylphenyl, ethylphenyl, 4-tert-butylphenyl and naphthyl.

In the invention, aralkyl refers to an alkyl group having an aryl substituent. Examples may include but are not limited to, phenylmethyl, phenylethyl, phenyl n-propyl, phenyl n-butyl, phenyl tert-butyl and phenyl isopropyl.

In the invention, alkaryl refers to an aryl group having an alkyl substituent with 7-20 carbon atoms, examples of which may include but are not limited to, methylphenyl and ethylphenyl.

In the invention, examples of alkoxyl may include but are not limited to, methoxy, ethoxy, n-propoxy, isopropoxy, n-butoxy, sec-butoxy, isobutoxy, isopropoxy, n-butoxy, sec-butoxy, isobutoxy, tert-butoxy, n-pentoxy, isopentoxy, tert-pentoxy, and hexyloxy.

In the invention, examples of fused ring aryl may include but are not limited to, naphthyl, anthracenyl, phenanthryl and pyrenyl.

In the invention, the heteroatom refers to an atom commonly contained in a molecular structure other than a halogen atom, a carbon atom and a hydrogen atom, such as O, N, S, P, Si, B, etc.

The beneficial effects of the invention:

When the catalyst system provided by the invention is used for olefin polymerization, the stereospecificity, catalytic activity and hydrogen modulation sensitivity are all relatively good. According to the above characteristics of the catalyst provided by the invention, the catalyst system provided by the invention is particularly suitable for preparing a polypropylene product with high stereoregularity and low ash, and the melt index of the product can be adjusted in a relatively wide range by adjusting the amount of hydrogenation. The catalyst system provided by the invention is also suitable for a copolymerization system to improve the copolymerization yield.

DETAILED DESCRIPTION OF THE EMBODIMENTS

The embodiments of the invention will be explained in details with reference to examples, but those skilled in the art will understand that the following examples are only used to illustrate the invention and should not be regarded as limiting the scope of the invention. If specific conditions are not indicated in an example, it shall be carried out in accordance with conventional conditions or conditions recommended by the manufacturer. If the manufacturer is not indicated for the reagents or instruments used, they are all conventional products that may be purchased commercially.

Test Methods:

1. Polymerization activity of the catalyst: it is obtained by dividing the amount of the polymer obtained in a certain period of time (in kg) with the amount of the catalyst added (in g).

2. Weight average molecular weight: it is measured by high temperature sol permeation chromatography with reference to the standard GB/T 36214.4-2018.

3. Isotactic index of the polymer: it is performed with reference to the standard GB/T 2412-2008.

4. Ethylene content: it is measured by Fourier Infrared Spectrometer VERTEX70.

Preparation Example 1

A mixed solution of 3,4-dimethoxybenzhydrol (5 g)/dichloromethane (20 mL) was dropwise added to a dichloromethane (200 mL) solution of trifluoroacetic acid (25 mL). After the dropwise addition was completed, the reaction continued in the ice bath for 4 hours. The reaction solution was neutralized with a sodium hydroxide solution. The organic phase was separated followed by complete drainage. The resulting product was washed with water and an organic solvent many times, and was recrystallized in chloroform (80 mL)/benzene (30 mL) to obtain 2.5 g of compound A.

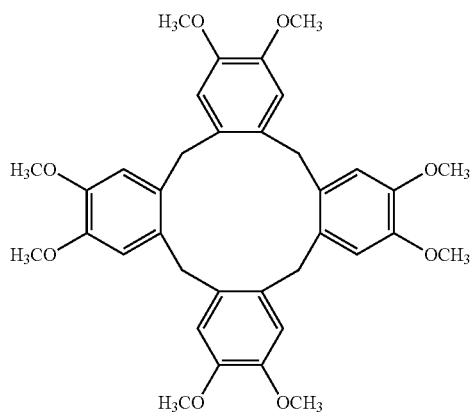

Compound A

Preparation Example 2

This preparation example is used to illustrate the preparation of a magnesium compound.

Anhydrous magnesium chloride and ethanol were mixed according to the molar ratio of 1:2.6, and the temperature was raised to 120° C. to perform the reaction so as to form a magnesium chloride alcoholate melt. The resulting melt was stirred in the dispersion media white oil and silicone oil at high speed and was then put into the cooled hexane to form spherical magnesium chloride alcoholate particles. The resulting particles were washed and dried to obtain a spherical magnesium chloride alcoholate carrier.

Preparation Example 3

This preparation example is used to illustrate the preparation of a solid catalyst component.

In a 300 ml glass reaction flask with stirring which had been fully displaced by high-purity nitrogen, 100 ml of titanium tetrachloride was added followed by cooling to −20° C. 8 g of the spherical magnesium chloride alcoholate prepared in the Preparation Example 2 was added followed by slowly raising the temperature to 110° C. In the temperature raising process, 6 mmol of 2-isopropyl-2-isopentyl-1,3-dimethoxypropane was added as an internal electron donor. After the temperature was kept at 110° C. for 0.5 h, the liquid was filtered off, and titanium tetrachloride was added for the treatment twice. Then, washing with hexane was performed five times. After drying in vacuum, titanium-containing solid catalyst component Z1 with titanium content of 2.4 wt % was obtained.

Preparation Example 4

This preparation example is used to illustrate the preparation of a solid catalyst component.

In a 300 ml glass reaction flask with stirring which had been fully displaced by high-purity nitrogen, 100 ml of titanium tetrachloride was added followed by cooling to −20° C. 8 g of the spherical magnesium chloride alcoholate prepared in the Preparation Example 2 was added followed by slowly raising the temperature to 110° C. In the temperature raising process, 3 mmol of 2,4-pentanediol dibenzoate and 3 mmol of 2-isopropyl-2-isopentyl-1,3-dimethoxypropane were added as internal electron donors. After the temperature was kept at 110° C. for 0.5 h, the liquid was filtered off, and titanium tetrachloride was added for the treatment twice. Then, washing with hexane was performed five times. After drying in vacuum, titanium-containing solid catalyst component Z2 with titanium content of 2.7 wt % was obtained.

Preparation Example 5

This preparation example is used to illustrate the preparation of a solid catalyst component.

In a reactor which had been fully displaced by high-purity nitrogen, 6.0 g of magnesium chloride, 119 ml of toluene, 5 ml of epichlorohydrin and 15.6 ml of tributyl phosphate (TBP) were added successively. The temperature was raised to 50° C. with stirring, then continue stirring at 50° C. for 2.5 hours, and the solid was completely dissolved. 1.7 g of phthalic anhydride was added, then continue stirring at 50° C. for 1 hour. The solution was cooled to below −25° C. 70 ml of $TiCl_4$ was dropwise added within 1 hour and the temperature was slowly raised to 80° C. In the temperature raising process, a solid was gradually precipitated. 6 mmol of 3-methyl-2,4-pentanediol dibenzoate was added as an internal electron donor, and the temperature was maintained for 1 hour. After filtration, 80 ml of toluene was added and washing was performed twice to obtain a solid precipitate. Then, 60 ml of toluene and 40 ml of $TiCl_4$ were added, and the temperature was raised to 100° C. The treatment was performed for 2 hours. After the filtrate was drained off, 60 ml of toluene and 40 ml of $TiCl_4$ were added again, and the temperature was raised to 100° C. The treatment was performed for 2 hours. The filtrate was drained off 60 ml of toluene was added. Washing was performed 3 times in a boiling state. 60 ml of hexane was then added. Washing was performed twice in a boiling state. 60 ml of hexane was added. After washing was performed twice at room temperature, solid catalyst component Z3 with titanium content of 2.5 wt % was obtained.

Preparation Example 6

This preparation example is used to illustrate the preparation of magnesium alkoxide.

After a 16 L pressure-resistant reactor with a stirrer was fully displaced with nitrogen, 10 L of ethanol, 300 mL of 2-ethylhexanol, 11.2 g of iodine, 8 g of magnesium chloride and 640 g of magnesium powder were added to the reactor. While stirring, the system was heated to 75° C. and refluxed for the reaction until no more hydrogen was discharged. The reaction was stopped. The mixture was washed with 3 L of ethanol, filtered, and dried to obtain magnesium alkoxide.

Preparation Example 7

This preparation example is used to illustrate the preparation of a solid catalyst component.

10 g of the magnesium alkoxide compound of the Preparation Example 6, 50 mL of toluene, 3 mmol of 2,3-diisopropyl diethyl succinate and 3 mmol of 3,5-heptanediol dibenzoate were taken and formulated into a suspension. In a 300 mL reaction kettle that had been repeatedly displaced by high-purity nitrogen, 40 mL of toluene and 60 mL of titanium tetrachloride were added. The temperature was raised to 80° C., and then the formulated suspension was added to the kettle. The temperature was kept constant for 1 hour, and was slowly raised to 110° C. The temperature was kept constant for 2 hours. After pressure filtration, a mixed solution of 78 mL of toluene and 52 mL of titanium tetrachloride was added followed by the stirring treatment at 110° C. for 1 hour. Such treatment was carried out 3 times. After pressure filtration, washing with hexane was performed 4 times in 150 mL each time. The pressure filtration and drying were performed to obtain solid catalyst component Z4 with titanium content of 2.5 wt %.

Preparation Example 8

A mixed solution of 3,4-diethoxybenzyl alcohol (5.8 g)/dichloromethane (20 mL) was dropwise added to a dichloromethane (200 mL) solution of trifluoroacetic acid (25 mL). After the dropwise addition was completed, the reaction continued in the ice bath for 4 hours. The reaction solution was neutralized with a sodium hydroxide solution. The organic phase was separated followed by complete drainage. The resulting product was washed with water and an organic solvent many times, and was recrystallized in chloroform (80 mL)/benzene (30 mL) to obtain 1.5 g of compound B.

Compound B

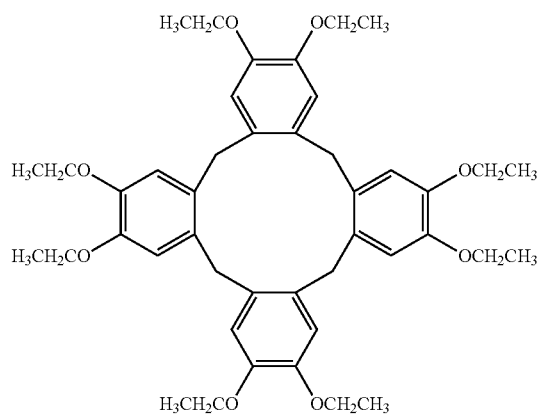

Preparation Example 9

A mixed solution of 3-methoxy-4-bromopropoxybenzyl alcohol (7 g)/dichloromethane (20 mL) was dropwise added to a dichloromethane (200 mL) solution of trifluoroacetic acid (25 mL). After the dropwise addition was completed, the reaction continued in the ice bath for 4 hours. The reaction solution was neutralized with a sodium hydroxide solution. The organic phase was separated followed by complete drainage. The resulting product was washed with water and an organic solvent many times, and was recrystallized in chloroform (80 mL)/benzene (30 mL) to obtain 1.7 g of compound P.

Compound P

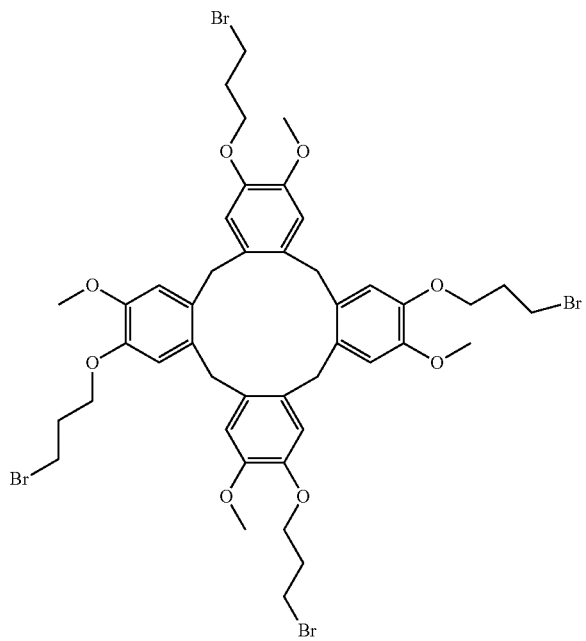

Preparation Example 10

A diethyl ether solution (100 mL) containing $P_2O_5$ (57.5 g) was stirred and dropwise added to a mixed solution of 3-iodo-4-methoxybenzhydrol (23 g)/diethyl ether. In reflux, stirring is stopped. 3 days later, the diethyl ether was spin-dried. The resulting product was dissolved in dichloromethane and passed through the column. After the filtrate was spin-dried, the resulting product was recrystallized with a mixed solution of diethyl ether/dichloromethane (95/5) to obtain 1.3 g of compound N.

Compound N

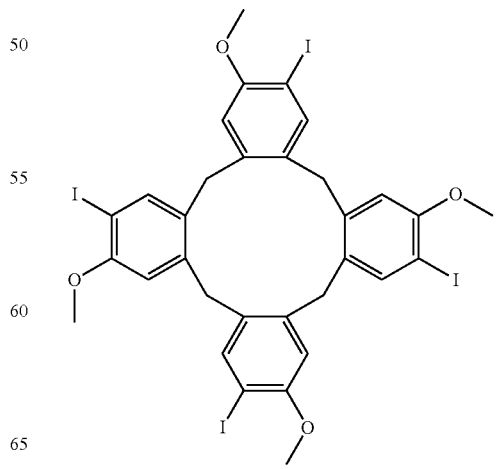

Preparation Example 11

2 mL of a toluene solution containing n-BuLi (5 mmol of n-BuLi) was added to 25 mL of a THF solution (containing 0.5 g of the compound N) at −80° C. After 1 hour, the reaction solution was heated to 0° C. After stirred at room temperature for 1 hour, the reaction solution was quickly cooled to −70° C. 2 mL of ethyl chloroformate was added. The reaction solution was returned to the room temperature and stirred for 3 hours. The remaining n-BuLi was neutralized with $NH_4Cl$. The organic phase was extracted with ethyl acetate, and 0.14 g of compound O was obtained after drying.

Compound O

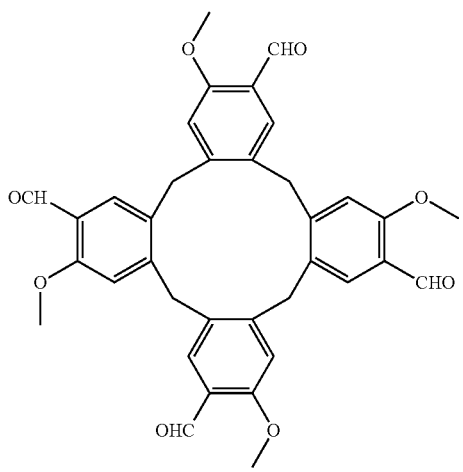

Example 1

4 mNL (mNL represents a milli standard liter) of hydrogen was added to a 48-channel parallel pressure reactor (the reaction volume is 20 ml). The reactor was filled with propylene gas to 1 MPa, and 5 ml of liquid propylene was added. According to the triethylaluminum (in terms of the aluminum element): compound A: solid catalyst component Z1 (in terms of the titanium element) molar ratio of 500:20:1, triethylaluminum, compound A, and a heptane solution of the solid catalyst component Z1 were added successively and formulated into a mixed solution. A certain amount of the mixed solution (containing 0.02 mg of the solid catalyst component) was taken and injected into the reactor. The reaction was performed at 70° C. for 1 hour.

The resulting product was discharged, and the weight of the polymer was weighed. The activity of the catalyst was obtained by calculation. Meanwhile, the isotactic index of the polymer was measured. The results are shown in Table 1.

Example 2

It is basically the same as Example 1, except that the amount of hydrogenation is 20 mNL. The results are shown in Table 1.

Example 3

It is basically the same as Example 1, except that the compound A is replaced with equimolar compound P. The results are shown in Table 1.

Example 4

It is basically the same as Example 2, except that the compound A is replaced with equimolar compound N. The results are shown in Table 1.

Comparative Example 1

It is basically the same as Example 1, except that the compound A is not added. The results are shown in Table 1.

Comparative Example 2

It is basically the same as Example 2, except that the compound A is not added. The results are shown in Table 1.

Comparative Example 3

It is basically the same as Example 2, except that the compound A is replaced with equimolar C-Donor. The results are shown in Table 1.

Example 5

It is basically the same as Comparative Example 3, except that compound A in an equimolar amount with the C-Donor is additionally added. The results are shown in Table 1.

Comparative Example 4

It is basically the same as Example 1, except that the compound A is replaced with equimolar Donor 1. The results are shown in Table 1.

Example 6

It is basically the same as Comparative Example 4, except that compound B in an equimolar amount with the Donor 1 is additionally added. The results are shown in Table 1.

Example 7

It is basically the same as Example 6, except that the solid catalyst component is replaced from Z1 to Z2, and the Donor 1 is replaced with equimolar C-Donor. The results are shown in Table 1.

Comparative Example 5

It is basically the same as Example 7, except that the compound B is not added. The results are shown in Table 1.

Example 8

It is basically the same as Example 7, except that the solid catalyst component is replaced from Z2 to Z4, and the amount of hydrogenation is changed to 20 mNL. The results are shown in Table 1.

Comparative Example 6

It is basically the same as Example 8, except that the compound B is not added. The results are shown in Table 1.

TABLE 1

| Example | Solid catalyst component | External electron donor | Cocatalyst | Amount of hydrogenation (mNL) | Activity (kgPP/gCat) | Isotactic index (%) |
|---|---|---|---|---|---|---|
| Example 1 | Z1 | — | Compound A | 4 | 65 | 98.7 |
| Example 2 | Z1 | — | Compound A | 20 | 69 | 95.9 |
| Example 3 | Z1 | — | Compound P | 4 | 68 | 97.6 |
| Example 4 | Z1 | — | Compound N | 20 | 69 | 95.8 |
| Comparative Example 1 | Z1 | — | — | 4 | 56 | 96.5 |
| Comparative Example 2 | Z1 | — | — | 20 | 63 | 95.3 |
| Example 5 | Z1 | C-Donor | Compound A | 20 | 72 | 96.3 |
| Comparative Example 3 | Z1 | C-Donor | — | 20 | 47 | 96.0 |
| Example 6 | Z1 | Donor 1 | Compound B | 4 | 65 | 98.9 |
| Comparative Example 4 | Z1 | Donor 1 | — | 4 | 41 | 97.5 |
| Example 7 | Z2 | C-Donor | Compound B | 4 | 115 | 97.1 |
| Comparative Example 5 | Z2 | C-Donor | — | 4 | 77 | 97.0 |
| Example 8 | Z4 | C-Donor | Compound B | 20 | 47 | 95.8 |
| Comparative Example 6 | Z4 | C-Donor | — | 20 | 35 | 95.5 |

Note:
C-Donor: cyclohexylmethyldimethoxysilane;
Donor 1: 2-isopropyl-2-isopentyl-1,3-dimethoxypropane.

It can be seen from Table 1 that for the catalyst system with or without an external electron donor, when it is used in the polymerization of propylene, the addition of the twelve-membered ring compound represented by the formula (M) as a cocatalyst can significantly improve the activity of the catalyst. In addition, the isotactic index of the polymerization product has also been improved.

Example 9

It is basically the same as Example 1, except that the compound A is replaced with equimolar compound B. The results are shown in Table 2.

Comparative Example 7

It is basically the same as Example 1, except that the compound A is replaced with equimolar C-Donor. The results are shown in Table 2.

Example 10

It is basically the same as Example 2, except that a part of the compound A is replaced with equimolar C-Donor. In this example, the molar ratio of the compound A to the C-Donor is 1:1. The results are shown in Table 2.

Example 11

It is basically the same as Example 2, except that a part of the compound A is replaced with equimolar C-Donor. In this example, the molar ratio of the compound A to the C-Donor is 1:9. The results are shown in Table 2.

Example 12

It is basically the same as Example 10, except that the compound A is replaced with equimolar compound B. The results are shown in Table 2.

Example 13

It is basically the same as Example 12, except that the C-Donor is replaced with equimolar Donor 1, and the amount of hydrogenation is changed to 4 mNL. The results are shown in Table 2.

Example 14

It is basically the same as Example 2, except that the solid catalyst component is replaced from Z1 to Z2. The results are shown in Table 2.

Example 15

It is basically the same as Example 10, except that the solid catalyst component is replaced from Z1 to Z2. The results are shown in Table 2.

Example 16

It is basically the same as Example 9, except that the solid catalyst component is replaced from Z1 to Z2. The results are shown in Table 2.

Example 17

It is basically the same as Example 16, except that the amount of hydrogenation is changed to 20 mNL. The results are shown in Table 2.

Example 18

It is basically the same as Example 13, except that the solid catalyst component is replaced from Z1 to Z2, and the Donor 1 is replaced with equimolar C-Donor. The results are shown in Table 2.

Example 19

It is basically the same as Example 18, except that the amount of hydrogenation is changed to 20 mNL. The results are shown in Table 2.

Comparative Example 8

It is basically the same as Comparative Example 5, except that the amount of hydrogenation is changed to 20 mNL. The results are shown in Table 2.

Example 20

It is basically the same as Example 9, except that the solid catalyst component is replaced from Z1 to Z3. The results are shown in Table 2.

Example 21

It is basically the same as Example 20, except that the amount of hydrogenation is changed to 20 mNL. The results are shown in Table 2.

Example 22

It is basically the same as Example 21, except that the compound B is replaced with equimolar compound O. The results are shown in Table 2.

Comparative Example 9

It is basically the same as Example 20, except that the compound B is replaced with equimolar C-Donor. The results are shown in Table 2.

Comparative Example 10

It is basically the same as Comparative Example 9, except that the amount of hydrogenation is changed to 20 mNL. The results are shown in Table 2.

Example 23

It is basically the same as Example 21, except that the solid catalyst component is replaced from Z3 to Z4. The results are shown in Table 2.

Example 24

It is basically the same as Example 12, except that the solid catalyst component is replaced from Z1 to Z4. The results are shown in Table 2.

TABLE 2

| Example | Solid catalyst component | External electron donor | Cocatalyst | Molar ratio of cocatalyst: external electron donor | Amount of hydrogenation (mNL) | Activity (kgPP/gCat) | Isotactic index (%) | Weight-average molecular weight (ten thousand) |
|---|---|---|---|---|---|---|---|---|
| Example 9 | Z1 | — | Compound B | — | 4 | 70 | 97.8 | 58 |
| Comparative Example 7 | Z1 | C-Donor | — | — | 4 | 42 | 97.6 | 61 |
| Example 10 | Z1 | C-Donor | Compound A | 1:1 | 20 | 78 | 96.5 | 42 |
| Example 11 | Z1 | C-Donor | Compound A | 1:9 | 20 | 70 | 96.2 | 43 |
| Example 12 | Z1 | C-Donor | Compound B | 1:1 | 20 | 96 | 95.8 | 36 |
| Comparative Example 3 | Z1 | C-Donor | — | — | 20 | 47 | 96.0 | 45 |
| Example 13 | Z1 | Donor 1 | Compound B | 1:1 | 4 | 60 | 98.7 | 58 |
| Comparative Example 4 | Z1 | Donor 1 | — | — | 4 | 41 | 97.5 | 60 |
| Example 14 | Z2 | — | Compound A | — | 20 | 103 | 96.2 | 37 |
| Example 15 | Z2 | C-Donor | Compound A | 1:1 | 20 | 109 | 96.6 | 44 |
| Example 16 | Z2 | — | Compound B | — | 4 | 82 | 96.7 | 80 |
| Example 17 | Z2 | — | Compound B | — | 20 | 119 | 95.3 | 45 |
| Example 18 | Z2 | C-Donor | Compound B | 1:1 | 4 | 113 | 97.1 | 70 |
| Example 19 | Z2 | C-Donor | Compound B | 1:1 | 20 | 120 | 95.8 | 46 |
| Comparative Example 5 | Z2 | C-Donor | — | — | 4 | 77 | 97.0 | 82 |
| Comparative Example 8 | Z2 | C-Donor | — | — | 20 | 86 | 96.4 | 48 |
| Example 20 | Z3 | — | Compound B | — | 4 | 45 | 98.8 | 78 |
| Example 21 | Z3 | — | Compound B | — | 20 | 50 | 98.0 | 57 |
| Example 22 | Z3 | — | Compound O | — | 20 | 43 | 97.5 | 55 |
| Comparative Example 9 | Z3 | C-Donor | — | — | 4 | 35 | 98.5 | 84 |
| Comparative Example 10 | Z3 | C-Donor | — | — | 20 | 37 | 97.8 | 60 |
| Example 23 | Z4 | — | Compound B | — | 20 | 51 | 95.4 | 50 |
| Example 24 | Z4 | C-Donor | Compound B | 1:1 | 20 | 44 | 96.0 | 52 |
| Comparative Example 6 | Z4 | C-Donor | — | — | 20 | 35 | 95.5 | 56 |

Note:
C-Donor: cyclohexylmethyldimethoxysilane;
Donor 1: 2-isopropyl-2-isopentyl-1,3-dimethoxypropane.

It can be seen from Table 2 that when the catalyst system provided by the invention is used for olefin polymerization, especially propylene polymerization, the stereospecificity, catalytic activity and hydrogen modulation sensitivity are all relatively good. Compared with a catalyst system containing a silane compound or a diether compound as an external electron donor, the catalyst system containing a twelve-membered ring compound represented by the formula (M) as a cocatalyst has improved hydrogen modulation sensitivity, significantly improved polymerization activity, and a relatively good isotactic index of the polymer. When the silane compound or the diether compound is added to the catalyst system as an external electron donor, the isotactic index of the product is further improved. According to the above characteristics of the catalyst provided by the invention, the catalyst system provided by the invention is particularly suitable for preparing a polypropylene product with high stereoregularity and low ash, and the melt index of the product may be adjusted in a relatively wide range by adjusting the amount of hydrogenation.

Example 25

A 48-channel parallel pressure reactor (the reaction volume is 20 ml) was displaced with hydrogen. The reactor was filled with propylene gas to 1 MPa, and 5 ml of liquid propylene was added. According to the triethylaluminum (in terms of the aluminum element): compound A: solid catalyst component (in terms of the titanium element) molar ratio of 250:25:1, triethylaluminum, compound A, and a heptane solution of the solid catalyst component Z1 were added successively and formulated into a mixed solution. A certain amount of the mixed solution (containing 0.02 mg of the solid catalyst component) was taken and injected into the reactor. The reaction was performed at 70° C. for 40 minutes. The system was displaced with a mixture of ethylene and propylene (the volume ratio of ethylene and propylene is 1:1), and the reaction was performed at 80° C. with a controlled pressure of 0.7 Mpa for 20 minutes.

The resulting product was discharged, and the weight of the polymer was weighed. The activity of the catalyst was obtained by calculation. Meanwhile, the ethylene content of the polymer was measured. The results are shown in Table 3.

Comparative Example 11

It is basically the same as Example 25, except that the compound A is replaced with equimolar C-donor. The results are shown in Table 3.

Example 26

It is basically the same as Example 25, except that a part of the compound A is replaced with equimolar C-Donor. In this example, the molar ratio of the compound A to the C-Donor is 1:1. The results are shown in Table 3.

Example 27

It is basically the same as Example 26, except that the molar ratio of the compound A to the C-Donor is 1:9. The results are shown in Table 3.

Example 28

It is basically the same as Example 25, except that the solid catalyst component Z1 is replaced with solid catalyst component Z2. The results are shown in Table 3.

Example 29

The only difference from Example 28 lies in that the compound A is replaced with equimolar compound B. The results are shown in Table 3.

Comparative Example 12

The only difference from Example 28 lies that the compound A is replaced with equimolar C-donor. The results are shown in Table 3.

TABLE 3

| Example | Solid catalyst component | External electron donor | Cocatalyst | Molar ratio of cocatalyst: external electron donor | Activity (kgPP/gCat) | Ethylene content (wt %) |
|---|---|---|---|---|---|---|
| Example 25 | Z1 | — | Compound A | — | 60 | 6.3 |
| Comparative Example 11 | Z1 | C-Donor | — | — | 42 | 6.4 |
| Example 26 | Z1 | C-Donor | Compound A | 1:1 | 80 | 6.3 |
| Example 27 | Z1 | C-Donor | Compound A | 1:9 | 76 | 6.3 |
| Example 28 | Z2 | — | Compound A | — | 80 | 4.6 |
| Example 29 | Z2 | — | Compound B | — | 100 | 4.5 |
| Comparative Example 12 | Z2 | C-Donor | — | — | 62 | 4.7 |

Note:
C-Donor: cyclohexylmethyldimethoxysilane; the ethylene content refers to content of a —$CH_2CH_2$— unit derived from an ethylene monomer in the polymer.

It can be seen from Table 3 that when the catalyst system provided by the invention is used for olefin copolymerization, especially ethylene and propylene copolymerization, compared with C-Donor as an external electron donor, the ethylene content of the copolymer obtained from the catalyst system containing the twelve-membered ring represented by the formula (M) as a cocatalyst, is equivalent, and the polymerization activity is improved. According to the above characteristics of the catalyst provided by the invention, the catalyst system provided by the invention is also suitable for a copolymerization system to improve the copolymerization yield.

It should be noted that the above-mentioned examples are only used to explain the invention, and do not constitute any limitation to the invention. The invention may be modified within the scope of the claims of the invention as stipulated, and the invention may be revised without departing from the scope and spirit of the invention. Although the invention described therein relates to specific methods, materials and examples, it does not mean that the invention is limited to the specific examples disclosed therein. On the contrary, the invention can be extended to all other methods and use with the same function.

The invention claimed is:

1. A catalyst system for olefin polymerization, comprising a main catalyst and a cocatalyst, wherein the cocatalyst comprises a twelve-membered ring compound represented by formula (M), Formula (M)

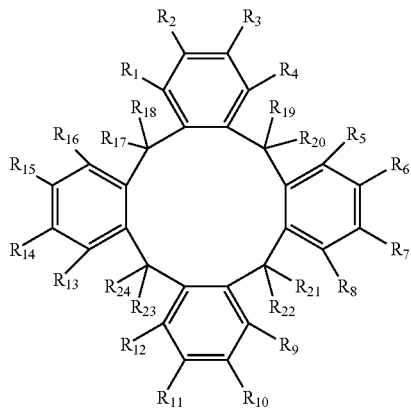

wherein in the formula (M), $R_1$-$R_{16}$ are the same or different, each independently selected from the group consisting of hydrogen, hydroxyl, halogen, cyano, nitro, amino, amine, aldehyde, carboxyl, ketone, alkoxy and hydrocarbyl, and when two adjacent groups on a benzene ring are each selected from the group consisting of alkoxy and hydrocarbyl, the two adjacent groups may optionally form a ring with each other, the ring selected from the group consisting of a saturated or unsaturated monocyclic ring, a saturated or unsaturated polycyclic ring and a combination thereof; and wherein $R_{17}$ to $R_{24}$ are the same or different, each independently selected from the group consisting of hydrogen and $C_1$-$C_{10}$ hydrocarbyl, and the amine, aldehyde, carboxyl, ketone, alkoxy and hydrocarbyl may be optionally substituted by one or more substituents.

2. The catalyst system according to claim 1, characterized in that the main catalyst comprises (i) a solid catalyst component containing magnesium, titanium, halogen and an internal electron donor compound; (ii) an organic aluminum compound; and optionally (iii) an external electron donor compound.

3. The catalyst system according to claim 2, characterized in that a molar ratio of the external electron donor compound to titanium element in the solid catalyst component is (0-500):1.

4. The catalyst system according to claim 1, characterized in that, in the formula (M), $R_1$-$R_{16}$ are the same or different, each independently selected from the group consisting of hydrogen, hydroxyl, halogen, cyano, nitro, amino, mono-$C_1$-$C_{10}$ alkyl amine, bis-$C_1$-$C_{10}$ alkyl amine, $C_1$-$C_{10}$ aldehyde, $C_1$-$C_{10}$ carboxyl, $R_aC(O)$—, $R_aO$—, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl, and when two adjacent groups on a benzene ring are each selected from the group consisting of $R_aC(O)$—, $R_aO$—, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl, the two adjacent groups may optionally form a ring with each other, the ring selected from the group consisting of a saturated or unsaturated monocyclic ring, a saturated or unsaturated polycyclic ring and a combination thereof, wherein $R_a$ is selected from the group consisting of $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, $C_7$-$C_{20}$ aralkyl, 4-12-membered heterocycloalkyl and $C_5$-$C_{20}$ heteroaryl; and $R_{17}$ to $R_{24}$ are the same or different, each independently selected from the group consisting of hydrogen, $C_1$-$C_{10}$ alkyl, $C_2$-$C_{10}$ alkenyl, $C_2$-$C_{10}$ alkynyl, $C_3$-$C_8$ cycloalkyl, $C_6$-$C_{10}$ aryl, $C_7$-$C_{20}$ aralkyl, 4-12-membered heterocycloalkyl and $C_5$-$C_{20}$ heteroaryl, and any one of the alkyl, alkenyl, alkynyl, cycloalkyl, aryl, aralkyl, heterocycloalkyl and heteroaryl may be optionally substituted by one or more substituents.

5. The catalyst system according to claim 1, characterized in that, in the formula (M), the substituents are selected from the group consisting of alkyl, alkoxyl, hydroxyl, halogen, cyano, nitro, amino, alkyl substituted amino, aldehyde, carboxyl and a heteroatom-containing group.

6. The catalyst system according to claim 1, characterized in that, in the formula (M), $R_1$ to $R_{16}$ are the same or different, and are each independently selected from the group consisting of hydrogen, hydroxyl, halogen, cyano, nitro, amino, mono-$C_1$-$C_6$ alkyl amine, bis-$C_1$-$C_6$ alkyl amine, $C_1$-$C_6$ aldehyde, $C_1$-$C_6$ carboxyl, $R_aC(O)$—, $R_aO$—, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $C_7$-$C_{10}$ aralkyl, 4-6-membered heterocycloalkyl and $C_5$-$C_{10}$ heteroaryl, wherein $R_a$ is selected from the group consisting of $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $C_7$-$C_{10}$ aralkyl, 4-6-membered heterocycloalkyl and $C_5$-$C_{10}$ heteroaryl.

7. The catalyst system according to claim 1, characterized in that, in the formula (M), $R_1$, $R_4$, $R_5$, $R_8$, $R_9$, $R_{12}$, $R_{13}$ and $R_{16}$ are each independently selected from the group consisting of hydrogen and $C_1$-$C_6$ alkyl; $R_2$, $R_3$, $R_6$, $R_7$, $R_{10}$, $R_{11}$, $R_{14}$ and $R_{15}$ are each independently selected from the group consisting of hydroxyl, amino, halogen, $C_1$-$C_6$ aldehyde, $C_1$-$C_6$ alkoxyl and halogen substituted $C_1$-$C_6$ alkoxyl.

8. The catalyst system according to claim 1, characterized in that, in the formula (M), $R_{17}$ to $R_{24}$ are each independently selected from the group consisting of hydrogen and $C_1$-$C_{10}$ alkyl.

9. The catalyst system according to claim 1, characterized in that, the twelve-membered ring compound represented by the formula (M) is represented by formula (N), Formula (N)

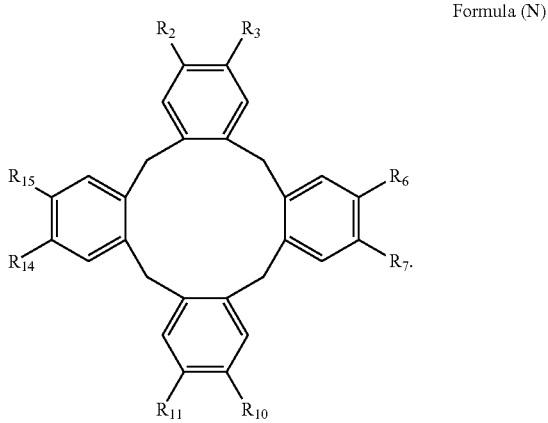

10. The catalyst system according to claim 2, characterized in that the internal electron donor compound is selected from one or more of a diether compound, an alcohol ester compound, an aromatic carboxylic acid ester compound, a succinate compound and a ketone compound.

11. The catalyst system according to claim 10, characterized in that, the alcohol ester compound is a glycol ester compound represented by formula B,

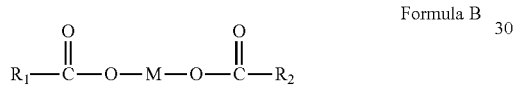

Formula B wherein, in the formula B, $R_1$ and $R_2$ are the same or different, each independently selected from the group consisting of $C_1$-$C_{20}$ alkyl, $C_2$-$C_{20}$ alkenyl, $C_3$-$C_{20}$ cycloalkyl, $C_6$-$C_{20}$ aryl, $C_7$-$C_{20}$ alkaryl, $C_7$-$C_{20}$ aralkyl and $C_{10}$-$C_{20}$ fused ring aryl, the alkyl, alkenyl, cycloalkyl, aryl, alkaryl, aralkyl and fused ring aryl optionally substituted by one or more substituents selected from the group consisting of $C_1$-$C_{10}$ alkyl, $C_1$-$C_{10}$ alkoxyl, hydroxyl, halogen, cyano, nitro, amino, mono-$C_1$-$C_6$ alkyl amine, bis-$C_1$-$C_6$ alkyl amine, aldehyde, carboxyl and a heteroatom; and M is a divalent linking group;
the diether compound is a 1,3-diether compound represented by formula E,

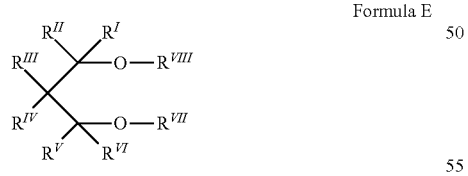

Formula E wherein, in the formula E, $R^I$, $R^{II}$, $R^{III}$, $R^{IV}$, $R^V$ and $R^{VI}$ are the same or different, and are each independently selected from the group consisting of hydrogen, halogen, $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl; $R^{VII}$ and $R^{VIII}$ are the same or different, and are each independently selected from the group consisting of $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, wherein any one of the alkyl, alkenyl, alkynyl, cycloalkyl, aryl, aralkyl and alkaryl may be optionally substituted by one or more substituents which are selected from the group consisting of hydroxyl, halogen, cyano, nitro, amino, mono-$C_1$-$C_{10}$ alkyl amine, bis-$C_1$-$C_{10}$ alkyl amine, aldehyde, carboxyl and a heteroatom; or, two or more of $R^I$, $R^{II}$, $R^{III}$, $R^{IV}$, $R^V$ and $R^{VI}$ are bonded to each other to form a saturated or unsaturated monocyclic or polycyclic ring;
a structure of the aromatic carboxylic acid ester compound is as shown in formula F:

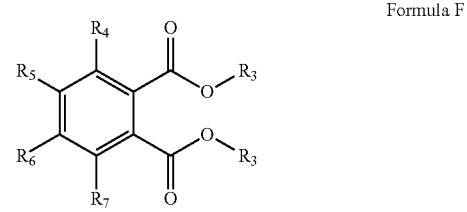

Formula F wherein, in the formula F, each $R_3$ is the same or different, which is independently $C_1$-$C_8$ alkyl, $C_5$-$C_{10}$ cycloalkyl, $C_6$-$C_{15}$ aryl, $C_7$-$C_{15}$ alkaryl or $C_7$-$C_{15}$ aralkyl, and hydrogen on carbon of the $C_1$-$C_8$ alkyl, $C_3$-$C_{10}$ branched alkyl, $C_5$-$C_{10}$ cycloalkyl, $C_6$-$C_{15}$ aryl, $C_7$-$C_{15}$ alkaryl or $C_7$-$C_{15}$ aralkyl may be optionally substituted by a substituent selected from the group consisting of an alkane and a halogen atom; and $R_4$-$R_7$ may be the same or different, which are hydrogen, halogen, $C_1$-$C_6$ alkyl, $C_5$-$C_{10}$ cycloalkyl, $C_6$-$C_{20}$ aryl, $C_7$-$C_{20}$ alkaryl or $C_7$-$C_{20}$ aralkyl, and hydrogen on carbon of the $C_1$-$C_8$ alkyl, $C_5$-$C_{10}$ cycloalkyl, $C_6$-$C_{15}$ aryl, $C_7$-$C_{15}$ alkaryl or $C_7$-$C_{15}$ aralkyl may be optionally substituted by a substituent selected from the group consisting of an alkane and a halogen atom; and
a structure of the succinate compound is as shown in formula G,

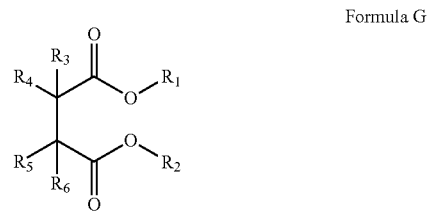

Formula G wherein, in the formula G, $R_1$ and $R_2$ are the same or different, each independently selected from the group consisting of a $C_1$-$C_{20}$ alkyl group, a $C_3$-$C_{20}$ cycloalkyl group, a $C_6$-$C_{20}$ aryl group, a $C_7$-$C_{20}$ arylalkyl group or a $C_7$-$C_{20}$ alkylaryl group, and optionally containing a heteroatom; and $R_3$, $R_4$, $R_5$ and $R_6$ are the same or different, each independently selected from the group consisting of hydrogen, a $C_1$-$C_{20}$ alkyl group, a cycloalkyl group, an aryl group, an arylalkyl group or an alkylaryl group, and optionally containing a heteroatom, and groups may be connected to form a ring.

12. The catalyst system according to claim 2, characterized in that, the external electron donor compound is selected from one or more of a silane compound, an ester compound, an ether compound and a ketone compound.

13. The catalyst system according to claim 12, characterized in that, a structure of the silane compound is shown in formula D:

Formula D

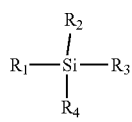

wherein in the formula D, $R_1$ to $R_4$ are the same or different, each independently selected from the group consisting of hydrogen, $C_1$-$C_{10}$ alkyl, $C_2$-$C_{10}$ alkenyl, $C_1$-$C_{10}$ alkoxyl, $C_2$-$C_{10}$ enyloxy, $C_2$-$C_{10}$ alkynyl, $C_2$-$C_{10}$ ynoxy, $C_3$-$C_{10}$ cycloalkyl, $C_6$-$C_{15}$ aryl, $C_3$-$C_{10}$ cycloalkoxyl, $C_6$-$C_{15}$ aryloxyl and amino, wherein the alkyl, alkenyl, alkynyl, alkoxyl, enyloxy, ynoxy, cycloalkyl, aryl, cycloalkoxyl, aryloxyl and amino may be optionally substituted by one or more substituents selected from the group consisting of halogen, $C_1$-$C_6$ alkyl, $C_3$-$C_6$ cycloalkyl, $C_6$-$C_{10}$ aryl and amino; and the ether compound is a 1,3-diether compound represented by formula E, Formula E

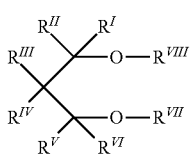

wherein, in the formula E, $R^I$, $R^{II}$, $R^{III}$, $R^{IV}$, $R^V$ and $R^{VI}$ are the same or different, and are each independently selected from the group consisting of hydrogen, halogen, $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl; $R^{VII}$ and $R^{VIII}$ are the same or different, and are each independently selected from the group consisting of $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, wherein any one of the alkyl, alkenyl, alkynyl, cycloalkyl, aryl, aralkyl and alkaryl may be optionally substituted by one or more substituents which are selected from the group consisting of hydroxyl, halogen, cyano, nitro, amino, mono-$C_1$-$C_{10}$ alkyl amine, bis-$C_1$-$C_{10}$ alkyl amine, aldehyde, carboxyl and a heteroatom; or, two or more of $R^I$, $R^{II}$, $R^{III}$, $R^{IV}$, $R^V$ and $R^{VI}$ and are bonded to each other to form a saturated or unsaturated monocyclic or polycyclic ring.

14. The catalyst system according to claim 2, characterized in that, a molar ratio of the twelve-membered ring compound represented by the formula (M) to the external electron donor compound is 1:100-100:1.

15. The catalyst system according to claim 2, characterized in that, the organic aluminum compound is an alkyl aluminum compound.

16. The catalyst system according to claim 2, characterized in that, a molar ratio of the twelve-membered ring compound represented by the formula (M) to the organic aluminum compound in terms of aluminum is 1:(0.1-500); and a molar ratio of the solid catalyst component in terms of titanium element to the organic aluminum compound in terms of aluminum is 1:(5-5000).

17. A prepolymerized catalyst composition for olefin polymerization, which comprises the catalyst system according to claim 1 and a prepolymer obtained by the olefin prepolymerization.

18. A method for olefin polymerization, comprising: polymerizing an olefin having a general formula of $CH_2$=CHR in the presence of the catalyst system according to claim 1, wherein R is hydrogen or $C_1$-$C_8$ alkyl.

19. A method for olefin polymerization, comprising: polymerizing an olefin having a general formula of $CH_2$=CHR in the presence of the prepolymerized catalyst composition according to claim 17, wherein R is hydrogen or $C_1$-$C_8$ alkyl.

20. The method for olefin polymerization according to claim 18, wherein R is hydrogen or $C_1$-$C_8$ alkyl, wherein the olefin is selected from one or more of ethylene, propylene, 1-butene, 4-methyl-1-pentene, and 1-hexene.

21. The catalyst system according to claim 3, characterized in that the molar ratio of the external electron donor compound to titanium element in the solid catalyst component is (0.01-200):1.

22. The catalyst system according to claim 5, characterized in that, in the formula (M), the substituents are selected from the group consisting of $C_1$-$C_{10}$ alkyl, $C_1$-$C_{10}$ alkoxyl, hydroxyl, halogen, cyano, nitro, amino, mono-$C_1$-$C_{10}$ alkyl amine, bis-$C_1$-$C_{10}$ alkyl amine, $C_1$-$C_{10}$ aldehyde, $C_1$-$C_{10}$ carboxyl and a heteroatom-containing group.

23. The catalyst system according to claim 6, characterized in that, in the formula (M), $R_1$ to $R_{16}$ are selected from the group consisting of hydrogen, hydroxyl, amino, halogen, $C_1$-$C_6$ aldehyde, $C_1$-$C_6$ alkoxyl and halogen substituted $C_1$-$C_6$ alkoxyl.

24. The catalyst system according to claim 9, characterized in that, the twelve-membered ring compound represented by the formula (M) is selected from one or more of the following compounds:

Compound A: in the formula (N), $R_2$=$R_3$=$R_6$=$R_7$=$R_{10}$=$R_{11}$=$R_{14}$=$R_{15}$=$OCH_3$;

Compound B: in the formula (N), $R_2$=$R_3$=$R_6$=$R_7$=$R_{10}$=$R_{11}$=$R_{14}$=$R_{15}$=$OCH_2CH_3$;

Compound C: in the formula (N), $R_2$=$R_3$=$R_6$=$R_7$=$R_{10}$=$R_{11}$=$R_{14}$=$R_{15}$=$OCH_2CH_2CH_3$;

Compound D: in the formula (N), $R_2$=$R_3$=$R_6$=$R_7$=$R_{10}$=$R_{11}$=$R_{14}$=$R_{15}$=$OCH(CH_3)_2$;

Compound E: in the formula (N), $R_2$=$R_3$=$R_6$=$R_7$=$R_{10}$=$R_{11}$=$R_{14}$=$R_{15}$=$OCH_2CH_2CH_2CH_3$;

Compound F: in the formula (N), $R_2$=$R_6$=$R_{10}$=$R_{14}$=$OCH_3$ and $R_3$=$R_7$=$R_{11}$=$R_{15}$=$OCH_2CH_3$;

Compound G: in the formula (N), $R_2$=$R_6$=$R_{10}$=$R_{14}$=$OCH_3$ and $R_3$=$R_7$=$R_{11}$=$R_{15}$=$OCH_2CH_2CH_3$;

Compound H: in the formula (N), $R_2$=$R_6$=$R_{10}$=$R_{14}$=$OCH_3$ and $R_3$=$R_7$=$R_{11}$=$R_{15}$=$OCH_2CH_2CH_2CH_3$;

Compound I: in the formula (N), $R_2$=$R_3$=$R_6$=$R_7$=$R_{10}$=$R_{11}$=$R_{14}$=$R_{15}$=$OH$;

Compound J: in the formula (N), $R_2$=$R_6$=$R_{10}$=$R_{14}$=$OCH_3$ and $R_3$=$R_7$=$R_{11}$=$R_{15}$=$OH$;

Compound K: in the formula (N), $R_2$=$R_6$=$R_{10}$=$R_{14}$=$OCH_3$ and $R_3$=$R_7$=$R_{11}$=$R_{15}$=$NH_2$;

Compound L: in the formula (N), $R_2$=$R_6$=$R_{10}$=$R_{14}$=$OCH_3$ and $R_3$=$R_7$=$R_{11}$=$R_{15}$=$Cl$;

Compound M: in the formula (N), $R_2$=$R_6$=$R_{10}$=$R_{14}$=$OCH_3$ and $R_3$=$R_7$=$R_{11}$=$R_{15}$=$Br$;

Compound N: in the formula (N), $R_2=R_6=R_{10}=R_{14}=OCH_3$ and $R_3=R_7=R_{11}=R_{15}=I$;

Compound O: in the formula (N), $R_2=R_6=R_{10}=R_{14}=OCH_3$ and $R_3=R_7=R_{11}=R_{15}=CHO$;

Compound P: in the formula (N), $R_2=R_6=R_{10}=R_{14}=OCH_3$ and $R_3=R_7=R_{11}=R_{15}=OCH_2CH_2CH_2Br$;

Compound Q: in the formula (N), $R_2=R_3=R_6=R_7=R_{10}=R_{11}=R_{14}=R_{15}=OCH_2CH_2Cl$; and Compound R: in the formula (N), $R_2=R_6=R_{10}=R_{14}=OH$ and $R_3=R_7=R_{11}=R_{15}=OCH_2CH_3$.

25. The catalyst system according to claim 11, characterized in that, wherein, in the formula B, $R_1$ and $R_2$ each independently selected from the group consisting of $C_1$-$C_{10}$ alkyl, $C_2$-$C_{10}$ alkenyl, $C_3$-$C_{10}$ cycloalkyl, $C_6$-$C_{10}$ aryl, $C_7$-$C_{10}$ alkaryl, $C_7$-$C_{10}$ aralkyl and $C_{10}$-$C_{15}$ fused ring aryl; and/or M is selected from the group consisting of $C_1$-$C_{20}$ alkylene, $C_3$-$C_{20}$ cycloalkylene and $C_6$-$C_{20}$ arylene, the alkylene, cycloalkylene and/or arylene substituted by a substituent selected from the group consisting of $C_1$-$C_{20}$ alkyl, $C_1$-$C_{20}$ alkoxyl and halogen, the substituent optionally bonded to form one or more rings, and a carbon atom or/and a hydrogen atom in M optionally substituted by a nitrogen, oxygen, sulfur, silicon, phosphorus or halogen atom;

and/or wherein, in the formula E, two or more of $R^I$, $R^{II}$, $R^{III}$, $R^{IV}$, $R^V$ and $R^{VI}$ are bonded to each other to form a fluorene ring.

26. The catalyst system according to claim 15, characterized in that, a general formula of the alkyl aluminum compound is $AlR_3$, wherein each R is independently selected from the group consisting of hydrogen, halogen, $C_1$-$C_{20}$ alkyl, $C_1$-$C_{20}$ alkoxyl or halogenated $C_1$-$C_{20}$ alkyl, and at least one of three Rs is $C_1$-$C_{20}$ alkyl.

27. The catalyst system according to claim 26, characterized in that, the general formula of the alkyl aluminum compound is $AlR_3$, wherein each R is independently selected from the group consisting of hydrogen, halogen, $C_1$-$C_{10}$ alkyl, $C_1$-$C_{10}$ alkoxyl or halogenated $C_1$-$C_{10}$ alkyl, and at least one of the three Rs is $C_1$-$C_{10}$ alkyl.

28. The catalyst system according to claim 17, characterized in that, a prepolymerization multiple of the prepolymer being 0.1-1000 g olefin polymer/g solid catalyst component.

* * * * *

UNITED STATES PATENT AND TRADEMARK OFFICE
CERTIFICATE OF CORRECTION

| | |
|---|---|
| PATENT NO. | : 11,840,508 B2 |
| APPLICATION NO. | : 17/629300 |
| DATED | : December 12, 2023 |
| INVENTOR(S) | : Jie Lin et al. |

It is certified that error appears in the above-identified patent and that said Letters Patent is hereby corrected as shown below:

In the Claims

In Claim 13, Column 35, Line 12 reading:
--$C_2$-$C_{10}$_ynoxy, $C_3$-$C_{10}$ cycloalkyl, $C_6$-$C_{is}$ aryl, $C_3$-$C_{10}$--
Should read:
--$C_2$-$C_{10}$ ynoxy, $C_3$-$C_{10}$ cycloalkyl, $C_6$-$C_{15}$ aryl, $C_3$-$Cl_0$--;

In Claim 13, Column 35, Line 46 reading:
--$R^{IV}$, $R^V$ and $R^{VI}$ and are bonded to each other to for--
Should read:
--$R^{IV}$, $R^V$ and $R^{VI}$ are bonded to each other to for--.

Signed and Sealed this
Seventh Day of May, 2024

Katherine Kelly Vidal
*Director of the United States Patent and Trademark Office*